(12) United States Patent
Uang et al.

(10) Patent No.: US 8,461,371 B2
(45) Date of Patent: Jun. 11, 2013

(54) METHOD OF ENANTIOSELECTIVE ADDITION TO IMINES

(75) Inventors: Biing-Jiun Uang, Hsinchu (TW); Wei-Ming Huang, Hsinchu (TW)

(73) Assignee: National Tsing Hua University, Hsinchu (TW)

( * ) Notice: Subject to any disclaimer, the term of this patent is extended or adjusted under 35 U.S.C. 154(b) by 332 days.

(21) Appl. No.: 12/899,092

(22) Filed: Oct. 6, 2010

(65) Prior Publication Data

US 2012/0004441 A1 Jan. 5, 2012

(30) Foreign Application Priority Data

Jul. 5, 2010 (TW) .................................. 99121992 A

(51) Int. Cl.
| | |
|---|---|
| *C07F 9/36* | (2006.01) |
| *C07F 9/46* | (2006.01) |
| *A01N 47/34* | (2006.01) |
| *C07C 337/00* | (2006.01) |
| *C07C 211/00* | (2006.01) |
| *C07C 17/42* | (2006.01) |
| *C09B 11/02* | (2006.01) |

(52) U.S. Cl.
USPC .............. 560/37; 564/12; 564/20; 564/323; 564/336; 570/113

(58) Field of Classification Search
None
See application file for complete search history.

(56) References Cited

PUBLICATIONS

Anderson, Pher G. et al.; "Preperation and Use of Aziridino Alcohols as Promoters for the Enantioselective Addition of Dialkylzinc Reagents to N-(Diphenylphosphinoyl) Imines"; 1997; J. of Org. Chem.; 62: pp. 7364-7375.*

Noyori, Ryoji et al.; "Enantioselective Addition of Organometallic Reagents to Carbonyl Compounds: Chirality Transfer, Multiplication, and Amplification"; 1991; Angew. Chem. Int. Ed. Engl.; 30: pp. 49-69.*

Soai, Kenso et al.; "Highly Enantioselective Alkylation of Carbon-Nitrogen Double Bonds. Catalytic and Stoichiometric Asymmetric synthesis of Optically Active Amines by the Enantioselective Addition of Dialkylzinc Reagents to N-Dipenylphosphinoylimines"; 1992; J. Chem. Soc., Chem. Commun.; pp. 1097-1098.*

* cited by examiner

*Primary Examiner* — Johann R Richter
*Assistant Examiner* — Blaine G Doletski
(74) *Attorney, Agent, or Firm* — Muncy, Geissler, Olds & Lowe, PLLC

(57) ABSTRACT

The present invention relates to a method of enantioselective addition to imines, including: reacting $R_3CH{=\!=}NY$ with $R_4ZnR_5$ in the presence of a compound represented by the following formula (I),

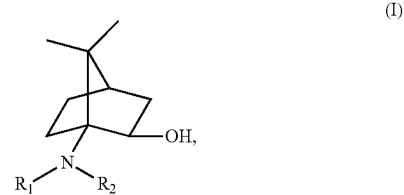

(I)

in which Y, $R_1$, $R_2$, $R_3$, $R_4$ and $R_5$ are defined the same as the specification. Accordingly, the present invention can prepare secondary amines in high yields and enantiomeric excess by the above-mentioned method.

13 Claims, No Drawings

METHOD OF ENANTIOSELECTIVE ADDITION TO IMINES

BACKGROUND OF THE INVENTION

1. Field of the Invention

The present invention relates to a method of enantioselective addition to imines and, more particularly, to a method of enantioselective addition of organozinc to imines using a chiral β-amino alcohol.

2. Description of Related Art

Most of isolated natural products have specific stereochemistry. Various stereoconfiguration causes significant difference in bioactivity, and particularly stereoconfiguration is critical for most drugs. For example, thalidomide is a chiral molecule and used for treating sickness and faintness of pregnant women, but its enantiomer causes abnormal fetal development; S,S-isomer of captopril is effective for treating of hypertension and heart disease; and S-isomer of Dopa can be used for treatment of Parkinson's disease, but its R-isomer has toxicity. The U.S. Food and Drug Administration, in 1992, issued that optical isomers of the drug having chiral center(s) should be isolated from each other, studied separately for their bioactivity and taken for clinical testing and only its therapeutically active isomer can be brought to market. Accordingly, many scientists have devoted themselves to the improvement of enantioselectivity to obtain substances having specific stereoconfiguration. The enantioselectivity of products may be enhanced by using chiral reagents, chiral auxiliaries or chiral catalysts, such that products can be synthesized in high optical activity.

Chiral amines play important roles in synthesis of bioactive substances and drugs. For example, methoxyphenamine is a β-adrenergic receptor agonist and can be used to treat asthma; rivastigmine is a pseudo-irreversible inhibitor of cholinesterase and can be used to treat Alzheimer's disease; tamsulosin is a selective α1-adrenoceptor antagonist and can be used to decrease urinary symptoms caused by prostate hypertrophy; and repaglinide can stimulate the release of insulin from the pancreas to reduce blood glucose and thus can be used in treating type II diabetes.

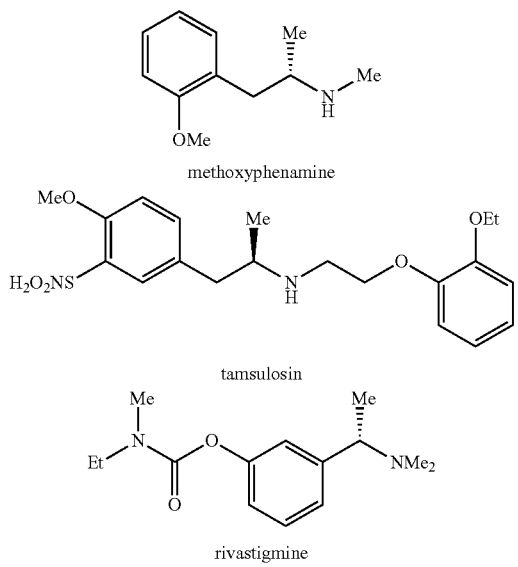

methoxyphenamine tamsulosin rivastigmine

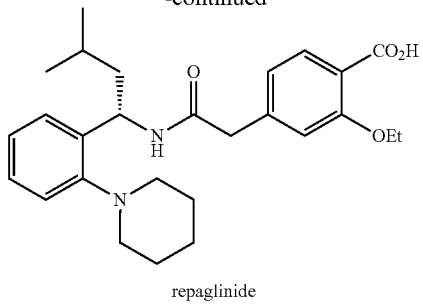

repaglinide

Accordingly, it is an important object of the present invention to develop a method for preparing amine products in high optical purity.

SUMMARY OF THE INVENTION

The object of the present invention is to provide a method of enantioselective addition to imines so as to synthesize amine products in high optical purity.

To achieve the object, the present invention provides a method of enantioselective addition to imines, including: reacting $R_3CH=NY$ with $R_4ZnR_5$ in the presence of a compound represented by the following formula (I),

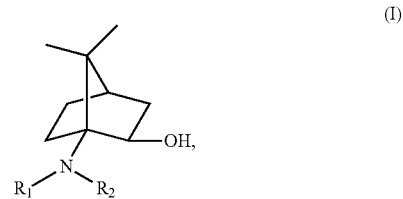

(I)

wherein each of $R_1$ and $R_2$ independently is alkyl, or $R_1$ and $R_2$ taken together is $(CH_2)_mX(CH_2)_n$; each of $R_3$, $R_4$ and $R_5$, independently, is alkyl, alkenyl, cycloalkyl, cycloalkenyl, heterocycloalkyl, heterocycloalkenyl, aryl, or heteroaryl; X is O, S or $CH_2$; Y is $P(O)Ph_2$; and each of m and n, independently, is 1, 2 or 3, and the sum of m and n is 3 or 4.

In detail, during the above-mentioned reaction, the compound represented by the formula (I) can be an auxiliary for enantioseletive addition of organozincs (i.e. $R_4ZnR_5$) to imines (i.e. $R_3CH=NY$). That is, the compound represented by the formula (I) can enhance enantioselectivity of addition, and one of the following formulas (II-1) and (II-2) may be prepared in the majority as the adduct:

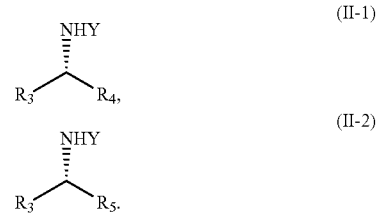

In the present invention, the term "alkyl" refers to a straight or branched hydrocarbon. Examples of alkyl include, but are not limited to, methyl, ethyl, n-propyl, i-propyl, n-butyl, i-butyl, and t-butyl.

In the present invention, the term "alkenyl" refers to a straight or branched hydrocarbon containing one or more double bonds. Examples of alkenyl include, but are not limited to, ethenyl, propenyl, allyl, and 1,4-butadienyl.

In the present invention, the term "cycloalkyl" refers to a saturated hydrocarbon ring system. Examples of cycloalkyl include, but are not limited to, cyclopropyl, cyclobutyl, cyclopentyl, cycloheptyl, and cyclooctyl.

In the present invention, the term "cycloalkenyl" refers to a non-aromatic hydrocarbon ring system having one or more double bonds. Examples of cycloalkenyl include, but are not limited to, cyclopentenyl, cyclohexenyl, and cycloheptenyl.

In the present invention, the term "heterocycloalkyl" refers to a saturated hydrocarbon ring system having one or more ring heteroatoms (e.g., N, O, S or Se). Examples of heterocycloalkyl include, but are not limited to, 4-tetrahydropyranyl.

In the present invention, the term "heterocycloalkenyl" refers to a non-aromatic hydrocarbon ring system having one or more ring heteroatoms (e.g., N, O, S or Se) and one or more ring double bonds. Examples of heterocycloalkenyl include, but are not limited to, pyranyl.

In the present invention, the term "aryl" refers to an aromatic ring system, which may be a 6-carbon monocyclic, 10-carbon bicyclic, 14-carbon tricyclic aromatic ring system. Examples of aryl groups include, but are not limited to, phenyl, naphthyl, and anthracenyl.

In the present invention, the term "heteroaryl" refers to aaromatic ring system having one or more heteroatoms (such as O, N, S, or Se), which may be a 5-8 membered monocyclic, 8-12 membered bicyclic, or 11-14 membered tricyclic aromatic ring system having one or more heteroatoms. Examples of heteroaryl groups include, but are not limited to, pyridyl, furyl, imidazolyl, benzimidazolyl, pyrimidinyl, thienyl, quinolinyl, indolyl, and thiazolyl.

The above-mentioned alkyl, alkenyl, cycloalkyl, cycloalkenyl, heterocycloalkyl, heterocycloalkenyl, aryl and heteroaryl include both substituted and unsubstituted moieties. The term "substituted" refers to one or more substituents (which may be the same or different), each replacing a hydrogen atom. Examples of substituents include, but are not limited to, halogen (such as F, Cl, Br or I), hydroxyl, amino, alkylamino, arylamino, dialkylamino, diarylamino, cyano, nitro, mercapto, carbonyl, carbamido, carbamyl, carboxyl, thiocyanato, sulfoamido, alkyl, alkenyl, alkoxy, haloalkyl (i.e. alkyl substituted by one or more halogen atoms), aryl, heteroaryl, cyclyl, heterocyclyl, $CO_2$-alkyl and $CO_2$-alkenyl. Among these above-mentioned substituents, alkyl, alkenyl, alkoxy, aryl, heteroaryl, cyclyl, and heterocyclyl may be optionally further substituted with, for example, alkyl, alkenyl, alkoxy, haloalkyl, aryl, heteroaryl, halogen, hydroxyl, amino, mercapto, cyano, nitro, $CO_2$-alkyl or $CO_2$-alkenyl.

Regarding $R_3CH=NY$, preferably, $R_3$ is unsubstituted or substituted $C_{1-30}$ alkyl by one or more selected from the group consisting of halogen, cyano, $C_{1-30}$ alkoxy, $C_{1-30}$ haloalkyl, $CO_2$—$C_{1-30}$ alkyl, $CO_2$—$C_{2-30}$ alkenyl, $C_{6-14}$ aryl and 5-14 membered heteroaryl; $(CH_2)_iR_a$; unsubstituted or substituted $C_{2-30}$ alkenyl by one or more selected from the group consisting of halogen, cyano, $C_{1-30}$ alkoxy, $C_{1-30}$ haloalkyl, $CO_2$—$C_{1-30}$ alkyl, $CO_2$—$C_{2-30}$ alkenyl, $C_{6-14}$ aryl and 5-14 membered heteroaryl; $(CH_2)_rCH=CH(CH_2)_kR_a$; unsubstituted or substituted $C_{5-14}$ cycloalkyl by one or more selected from the group consisting of halogen, cyano, $C_{1-30}$ alkyl, $C_{2-30}$ alkenyl, $C_{1-30}$ alkoxy, $C_{1-30}$ haloalkyl, $CO_2$—$C_{1-30}$ alkyl and $CO_2$—$C_{2-30}$ alkenyl; unsubstituted or substituted $C_{5-14}$ cycloalkenyl by one or more selected from the group consisting of halogen, cyano, $C_{1-30}$ alkyl, $C_{2-30}$ alkenyl, $C_{1-30}$ alkoxy, $C_{1-30}$ haloalkyl, $CO_2$—$C_{1-30}$ alkyl and $CO_2$—$C_{2-30}$ alkenyl; unsubstituted or substituted 5-1.4 membered heterocycloalkyl by one or more selected from the group consisting of halogen, cyano, $C_{1-30}$ alkyl, $C_{2-30}$ alkenyl, $C_{1-30}$ alkoxy, $C_{1-30}$ haloalkyl, $CO_2$—$C_{1-30}$ alkyl and $CO_2$—$C_{2-30}$ alkenyl; unsubstituted or substituted 5-14 membered heterocycloalkenyl by one or more selected from the group consisting of halogen, cyano, $C_{1-30}$ alkyl, $C_{2-30}$ alkenyl, $C_{1-30}$ alkoxy, $C_{1-30}$ haloalkyl, $CO_2$—$C_{1-30}$ alkyl and $CO_2$—$C_{2-30}$ alkenyl; unsubstituted or substituted $C_{6-14}$ aryl by one or more selected from the group consisting of halogen, cyano, $C_{1-30}$ alkyl, $C_{2-30}$ alkenyl, $C_{1-30}$ alkoxy, $C_{1-30}$ haloalkyl, $CO_2$—$C_{1-30}$ alkyl and $CO_2$—$C_{2-30}$ alkenyl; or unsubstituted or substituted 5-14 membered heteroaryl by one or more selected from the group consisting of halogen, cyano, $C_{1-30}$ alkyl, $C_{2-30}$ alkenyl, $C_{1-30}$ alkoxy, $C_{1-30}$ haloalkyl, $CO_2$—$C_{1-30}$ alkyl and $CO_2$—$C_{2-30}$ alkenyl; $R_a$ is substituted $C_{6-14}$ aryl by one or more selected from the group consisting of halogen, cyano, $C_{1-30}$ alkyl, $C_{2-30}$ alkenyl, $C_{1-30}$ alkoxy, $C_{1-30}$ haloalkyl, $CO_2$—$C_{1-30}$ alkyl and $CO_2$—$C_{2-30}$ alkenyl; or substituted 5-14 membered heteroaryl by one or more selected from the group consisting of halogen, cyano, $C_{1-30}$ alkyl, $C_{2-30}$ alkenyl, $C_{1-30}$ alkoxy, $C_{1-30}$ haloalkyl, $CO_2$—$C_{1-30}$ alkyl and $CO_2$—$C_{2-30}$ alkenyl; i is an integer of 1 to 30; and each of r and k independently is an integer of 0 to 30.

Regarding $R_3CH=NY$, more preferably, $R_3$ is unsubstituted or substituted $C_{1-10}$ alkyl by one or more selected from the group consisting of $C_{6-14}$ aryl and 5-14 membered heteroaryl; $(CH_2)_iR_a$; unsubstituted or substituted $C_{2-10}$ alkenyl by one or more selected from the group consisting of $C_{6-14}$ aryl and 5-14 membered heteroaryl; $(CH_2)_rCH=CH(CH_2)_kR_a$; unsubstituted $C_{5-14}$ cycloalkyl; unsubstituted $C_{5-14}$ cycloalkenyl; unsubstituted or substituted $C_{6-14}$ aryl by one or more selected from the group consisting of halogen, cyano, $C_{1-10}$ alkyl, $C_{2-10}$ alkenyl, $C_{1-10}$ alkoxy, $C_{1-10}$ haloalkyl, $CO_2$—$C_{1-10}$ alkyl and $CO_2$—$C_{2-10}$ alkenyl; or unsubstituted or substituted 5-14 membered heteroaryl by one or more selected from the group consisting of halogen, cyano, $C_{1-10}$ alkyl, $C_{2-10}$ alkenyl, $C_{1-10}$ alkoxy, $C_{1-10}$ haloalkyl, $CO_2$—$C_{1-10}$ alkyl and $CO_2$—$C_{2-10}$ alkenyl; $R_a$ is substituted $C_{6-14}$ aryl by one or more selected from the group consisting of halogen, cyano, $C_{1-10}$ alkyl, $C_{2-10}$ alkenyl, $C_{1-10}$ alkoxy, $C_{1-10}$ haloalkyl, $CO_2$—$C_{1-10}$ alkyl and $CO_2$—$C_{2-10}$ alkenyl; or substituted 5-14 membered heteroaryl by one or more selected from the group consisting of halogen, cyano, $C_{1-10}$ alkyl, $C_{2-10}$ alkenyl, $C_{1-10}$ alkoxy, $C_{1-10}$ haloalkyl, $CO_2$—$C_{1-10}$ alkyl and $CO_2$—$C_{2-10}$ alkenyl; i is an integer of 1 to 10; and each of r and k independently is an integer of 0 to 10.

Regarding $R_3CH=NY$, most preferably, $R_3$ is unsubstituted $C_{1-10}$ alkyl (e.g. $(CH_2)_{0-9}CH_3$); substituted $C_{1-10}$ alkyl by phenyl or naphthyl (e.g. $CH_2CH_2C_6H_5$ or $CH_2CH_2C_{10}H_7$); unsubstituted $C_{2-10}$ alkenyl (e.g. $(CH_2)_{0-8}CH=CH$); substituted $C_{2-10}$ alkenyl by phenyl or naphthyl (e.g. $CH=CHC_6H_5$, $CH=CHC_{10}H_7$, $CH_2CH=CHC_6H_5$ or $CH_2CH=CHC_{10}H_7$); unsubstituted $C_{5-10}$ cycloalkyl (e.g. cyclohexyl); unsubstituted $C_{5-10}$ cycloalkenyl; unsubstituted phenyl or naphthyl; substituted phenyl or naphthyl by one or more selected from the group consisting of halogen, cyano, $C_{1-10}$ alkyl (e.g. $(CH_2)_{0-9}CH_3$), $C_{2-10}$ alkenyl (e.g. $(CH_2)_{0-8}CH=CH_2$), $C_{1-10}$ alkoxy (e.g. $O(CH_2)_{0-9}CH_3$), $C_{1-10}$ haloalkyl (e.g. $(CH_2)_{0-9}CF_3$, $(CH_2)_{0-9}CCl_3$, $(CH_2)_{0-9}CBr_3$), $CO_2$—$C_{1-10}$ alkyl (e.g. $CO_2(CH_2)_{0-9}CH_3$) and $CO_2$—$C_{2-10}$ alkenyl (e.g. $CO_2(CH_2)_{0-7}CH=CH_2$), in which a substitute on phenyl is preferably at meta- or para-position; $(CH_2)_iR_a$; or $(CH_2)_rCH=CH(CH_2)_kR_a$, in which $R_a$ is substituted phenyl or naphthyl by one or more selected from the group consisting of halogen, cyano, $C_{1-10}$ alkyl, $C_{2-10}$ alkenyl, $C_{1-10}$ alkoxy, $C_{1-10}$ haloalkyl, $CO_2$—$C_{1-10}$ alkyl and $CO_2$—$C_{2-10}$ alkenyl; i is an integer of 1 to 10; and each of r and k independently is an integer of 0 to 8, and the sum of r and k is 8 (e.g. $CH_2CH_2C_6H_4CH_3$, $CH_2CH_2C_{10}H_6CH_3$, $CH=CHC_6H_4CH_3$, $CH=CHC_{10}H_6CH_3$, $CH_2CH=CHC_6H_4CH_3$ or $CH_2CH=CHC_{10}H_6CH_3$).
Examples of $R_3CH=NY$ include, but are not limited to,
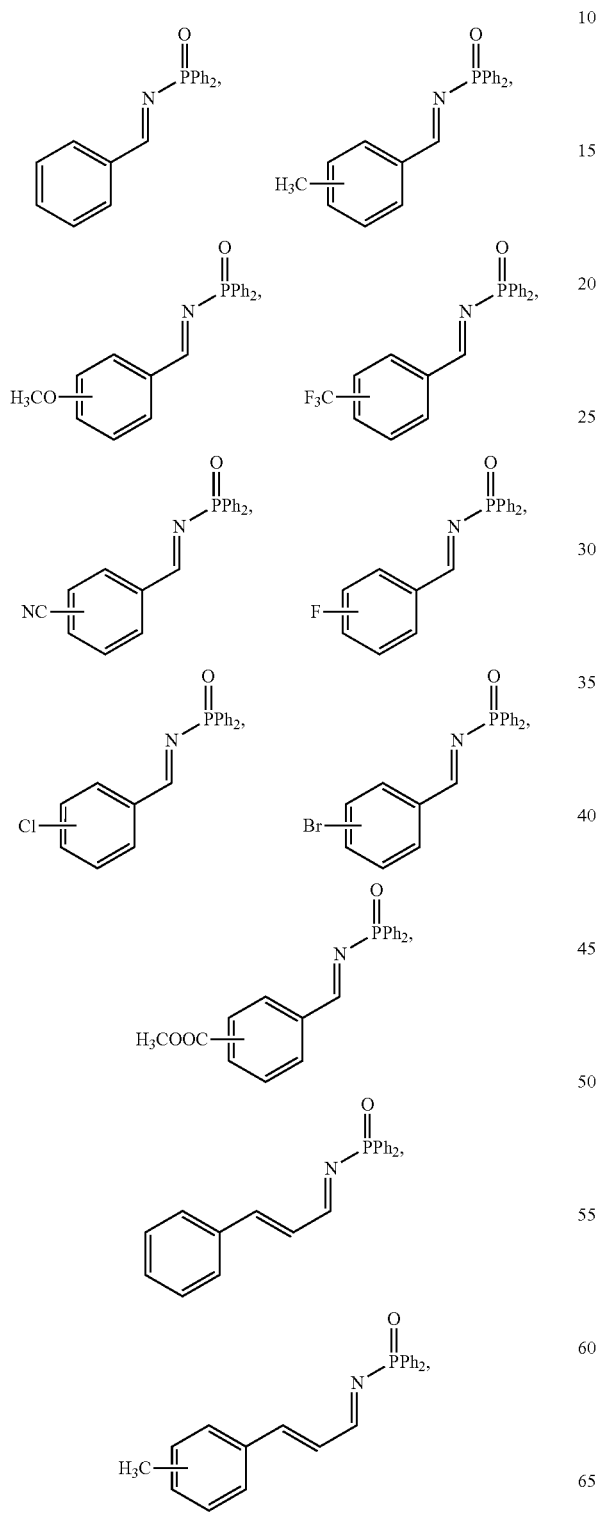
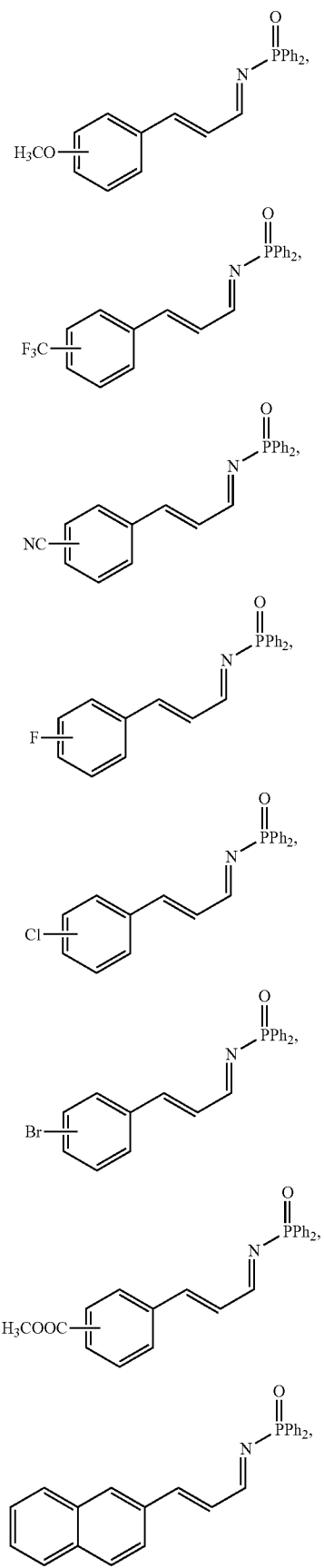

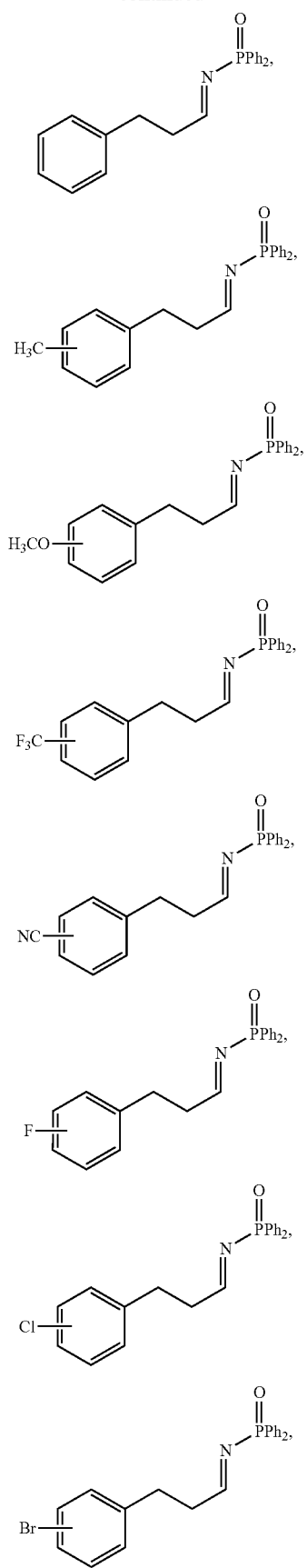
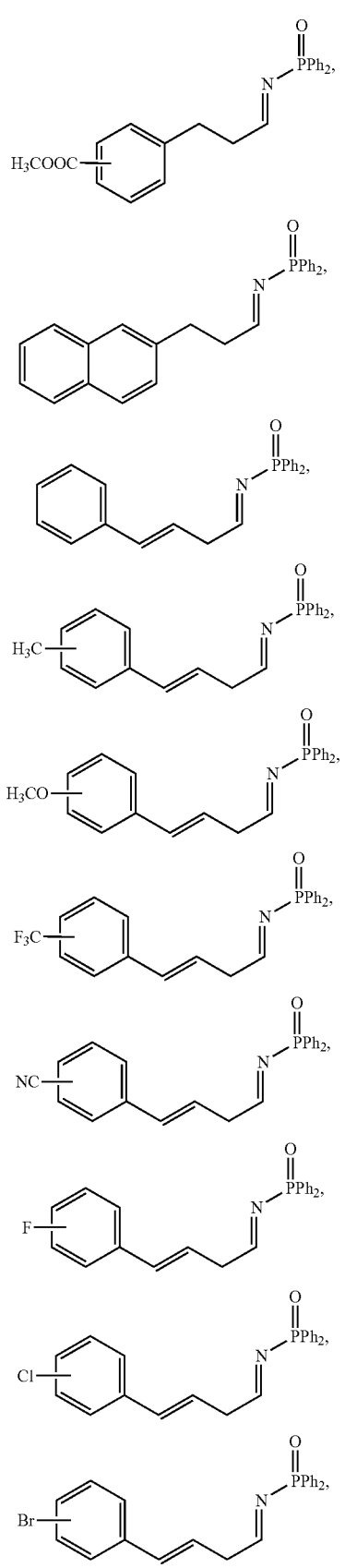

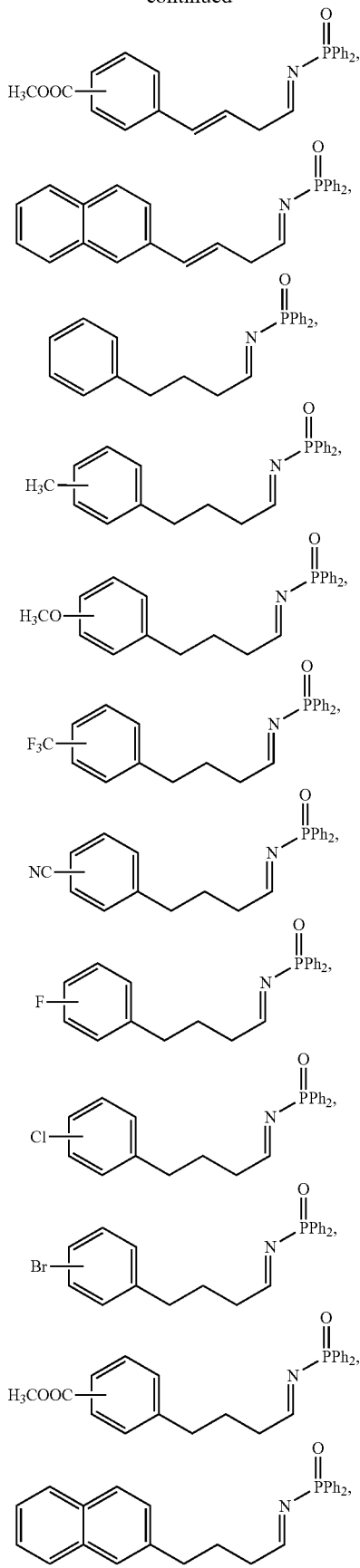

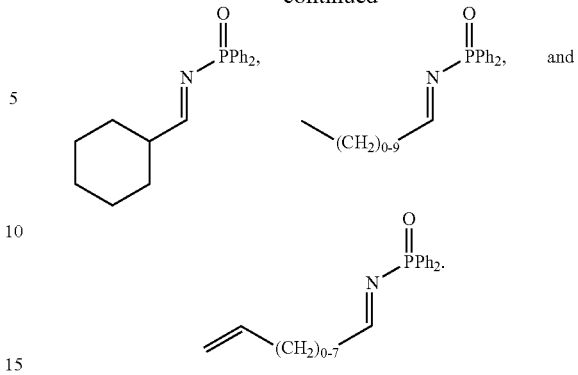

Regarding $R_4ZnR_5$, preferably, each of $R_4$ and $R_5$ independently is unsubstituted or substituted $C_{1-30}$ alkyl by one or more of halogen, cyano, $C_{1-30}$ alkoxy, $C_{1-30}$ haloalkyl, $CO_2$—$C_{1-30}$ alkyl, $CO_2$—$C_{2-30}$ alkenyl, $C_{6-14}$ aryl and 5-14 membered heteroaryl; unsubstituted or substituted $C_{2-30}$ alkenyl by one or more of halogen, cyano, $C_{1-30}$ alkoxy, $C_{1-30}$ haloalkyl, $CO_2$—$C_{1-30}$ alkyl, $CO_2$—$C_{2-30}$ alkenyl, $C_{6-14}$ aryl and $C_{5-14}$ heteroaryl; unsubstituted or substituted $C_{5-14}$ cycloalkyl by one or more of halogen, cyano, $C_{1-30}$ alkyl, $C_{2-30}$ alkenyl, $C_{1-30}$ alkoxy, $C_{1-30}$ haloalkyl, $CO_2$—$C_{1-30}$ alkyl and $CO_2$—$C_{2-30}$ alkenyl; unsubstituted or substituted $C_{5-14}$ cycloalkenyl by one or more of halogen, cyano, $C_{1-30}$ alkyl, $C_{2-30}$ alkenyl, $C_{1-30}$ alkoxy, $C_{1-30}$ haloalkyl, $CO_2$—$C_{1-30}$ alkyl and $CO_2$—$C_{2-30}$ alkenyl; unsubstituted or substituted 5-14 membered heterocycloalkyl by one or more of halogen, cyano, $C_{1-30}$ alkyl, $C_{2-30}$ alkenyl, $C_{1-30}$ alkoxy, $C_{1-30}$ haloalkyl, $CO_2$—$C_{1-30}$ alkyl and $CO_2$—$C_{2-30}$ alkenyl; unsubstituted or substituted 5-14 membered heterocycloalkenyl by one or more of halogen, cyano, $C_{1-30}$ alkyl, $C_{2-30}$ alkenyl, $C_{1-30}$ alkoxy, $C_{1-30}$ haloalkyl, $CO_2$—$C_{1-30}$ alkyl and $CO_2$—$C_{2-30}$ alkenyl; unsubstituted or substituted $C_{6-14}$ aryl by one or more of halogen, cyano, $C_{1-30}$ alkyl, $C_{2-30}$ alkenyl, $C_{1-30}$ alkoxy, $C_{1-30}$ haloalkyl, $CO_2$—$C_{1-30}$ alkyl and $CO_2$—$C_{2-30}$ alkenyl; or unsubstituted or substituted 5-14 membered heteroaryl by one or more of halogen, cyano, $C_{1-30}$ alkyl, $C_{2-30}$ alkenyl, $C_{1-30}$ alkoxy, $C_{1-30}$ haloalkyl, $CO_2$—$C_{1-30}$ alkyl and $CO_2$—$C_{2-30}$ alkenyl;

$R_a$ is substituted $C_{6-14}$ aryl by one or more selected from the group consisting of halogen, cyano, $C_{1-30}$ alkyl, $C_{2-30}$ alkenyl, $C_{1-30}$ alkoxy, $C_{1-30}$ haloalkyl, $CO_2$—$C_{1-30}$ alkyl and $CO_2$—$C_{2-30}$ alkenyl; or substituted 5-14 membered heteroaryl by one or more selected from the group consisting of halogen, cyano, $C_{1-30}$ alkyl, $C_{2-30}$ alkenyl, $C_{1-30}$ alkoxy, $C_{1-30}$ haloalkyl, $CO_2$—$C_{1-30}$ alkyl and $CO_2$—$C_{2-30}$ alkenyl.

Regarding $R_4ZnR_5$, more preferably, $R_4$ is unsubstituted $C_{1-10}$ alkyl; and $R_5$ is unsubstituted or substituted $C_{1-10}$ alkyl by one or more selected from the group consisting of $C_{6-14}$ aryl and 5-14 membered heteroaryl; unsubstituted or substituted $C_{2-10}$ alkenyl by one or more selected from the group consisting of $C_{6-14}$ aryl and 5-14 membered heteroaryl; unsubstituted $C_{5-14}$ cycloalkyl; unsubstituted $C_{5-14}$ cycloalkenyl; unsubstituted or substituted $C_{6-14}$ aryl by one or more selected from the group consisting of halogen, cyano, $C_{1-10}$ alkyl, $C_{2-10}$ alkenyl, $C_{1-10}$ alkoxy, $C_{1-10}$ haloalkyl, $CO_2$—$C_{1-10}$ alkyl and $CO_2$—$C_{2-10}$ alkenyl; unsubstituted or substituted 5-14 membered heteroaryl by one or more selected from the group consisting of halogen, cyano, $C_{1-10}$ alkyl, $C_{2-10}$ alkenyl, $C_{1-10}$ alkoxy, $C_{1-10}$ haloalkyl, $CO_2$—$C_{1-10}$ alkyl and $CO_2$—$C_{2-10}$ alkenyl.

Regarding $R_4ZnR_5$, most preferably, $R_4$ is unsubstituted $C_{1-10}$ alkyl (e.g. $(CH_2)_{0-9}CH_3$); and $R_5$ is unsubstituted $C_{1-10}$ alkyl (e.g. $(CH_2)_{0-9}CH_3$); unsubstituted $C_{2-10}$ alkenyl (e.g. $C(C_2H_5)=CH(C_2H_5)$, $CH=CHC(CH_3)_3$, $CH=CH(CH_2)_{0-7}CH_3$); substituted $C_{2-10}$ alkenyl by phenyl or naphthyl (e.g. $CH=CH(CH_2)_{0-8}C_6H_5$, $CH=CH(CH_2)_{0-8}C_{10}H_7$); unsubstituted phenyl or naphthyl; or substituted phenyl or naphthyl by one or more selected from the group consisting of halogen, cyano, $C_{1-10}$ alkyl (e.g. $(CH_2)_{0-9}CH_3$), $C_{2-10}$ alkenyl (e.g. $(CH_2)_{0-8}CH=CH_2$), $C_{1-10}$ alkoxy (e.g. $O(CH_2)_{0-9}CH_3$), $C_{1-10}$ haloalkyl (e.g. $(CH_2)_{0-9}CF_3$, $(CH_2)_{0-9}CCl_3$, $(CH_2)_{0-9}CBr_3$), $CO_2-C_{1-10}$ alkyl (e.g. $CO_2(CH_2)_{0-9}CH_3$) and $CO_2-C_{2-10}$ alkenyl (e.g. $CO_2(CH_2)_{0-8}CH=CH_2$).

Examples of $R_4ZnR_5$ include, but are not limited to, $Zn(CH_3)_2$, $Zn(C_2H_5)_2$,

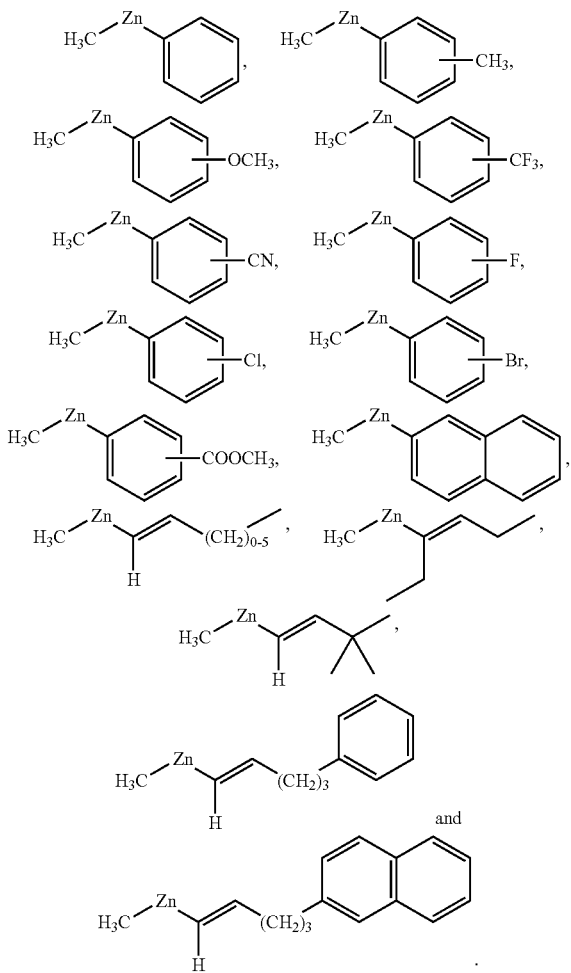

Regarding the compound represented by the formula (I), preferably, the sum of m and n is 4 when X is O or S.

Regarding the compound represented by the formula (I), preferably, m is 1 or 2 and n is 2.

Regarding the compound represented by the formula (I), preferably, X is O or $CH_2$.

Regarding the compound represented by the formula (I), preferably, each of $R_1$ and $R_2$ independently is $C_{1-30}$alkyl, or $R_1$ and $R_2$ taken together is $(CH_2)_mX(CH_2)_n$; more preferably, each of $R_1$ and $R_2$ independently is $C_{1-10}$ alkyl, or $R_1$ and $R_2$ taken together is $(CH_2)_mX(CH_2)_n$; and most preferably, each of $R_1$ and $R_2$ independently is $C_{1-10}$ alkyl, or $R_1$ and $R_2$ taken together is $(CH_2)_4$, $(CH_2)_5$ or $(CH_2)_2O(CH_2)_2$.

In the method of enantioselective addition according to the present invention, the compound represented by the formula (I) may be used in an amount from 0.1 to 1 equivent, preferably from 0.25 to 1 equivent, more preferably from 0.5 to 1 equivent, and most preferably from 0.6 to 1 equivent based on $R_3CH=NY$.

In the method of enantioselective addition according to the present invention, $R_3CH=NY$ may be reacted with $R_4ZnR_5$ at a temperature in a range from 0° C. to 50° C., and preferably from 0° C. to 25° C.

In the method of enantioselective addition according to the present invention, $R_4ZnR_5$ may be used in an amount from 1 to 10 equivents, preferably from 2 to 6 equivents, and more preferably from 3 to 6 equivents based on $R_3CH=NY$.

In the method of enantioselective addition according to the present invention, $R_3CH=NY$ may be reacted with $R_4ZnR_5$ in a solvent, and preferably in an aprotic solvent. Herein, the aprotic solvent may be selected from the group consisting of n-hexane, toluene, dichloromethane, tetrahydrofuran, acetonitrile, a mixture of n-hexane and toluene, a mixture of n-hexane and dichloromethane, a mixture of n-hexane and tetrahydrofuran, and a mixture of n-hexane and acetonitrile. Preferably, the aprotic solvent may be selected from the group consisting of n-hexane, toluene, a mixture of n-hexane and toluene in a ratio of 1:1 to 1:5, a mixture of n-hexane and dichloromethane in a ratio of 1:1 to 1:3, a mixture of n-hexane and tetrahydrofuran in a ratio of 1:1 to 1:3, and a mixture of n-hexane and acetonitrile in a ratio of 1:1 to 1:3.

In the method of enantioselective addition according to the present invention, the concentration of $R_3CH=NY$ in the aprotic solvent may range from 0.01 M to 1 M, preferably from 0.057 M to 0.6 M, and more preferably from 0.057 M to 0.55 M.

Accordingly, the present invention uses the above-mentioned compound represented by the formula (I) to perform enantioselective addition of organozincs to imines, so as to prepare secondary amines in high yield and enantiomeric excess (ee).

BRIEF DESCRIPTION OF THE DRAWINGS

None.

DETAILED DESCRIPTION OF THE PREFERRED EMBODIMENT

Preparation Example 1

Synthesis of β-amino Alcohols 5, 6 and 7

Scheme 1. Synthesis of β-amino alcohols 5, 6 and 7

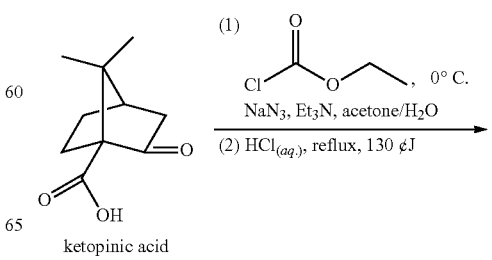

ketopinic acid

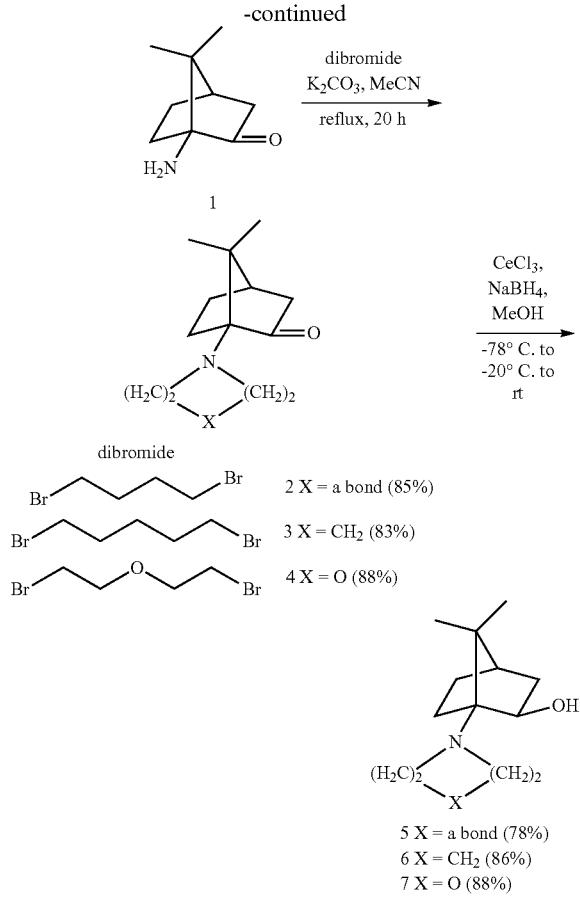

2 X = a bond (85%)
3 X = CH₂ (83%)
4 X = O (88%)

5 X = a bond (78%)
6 X = CH₂ (86%)
7 X = O (88%)

The β-amino alcohol ligands 5-7 were synthesized from ketopinic acid in three steps (Scheme 1). Ketopinic acid was reacted with ethyl chloroformate to form amine ketone 1. Subsequently, treatment of amine ketone 1 with 1,4-butane dibromide, 1,5-pentane dibromide, and bis-(2-bromoethyl) ether gave amino ketones 2-4, respectively. Finally, the diastereoselective reduction of amino ketones 2-4 with NaBH₄/CeCl₃ yielded the corresponding exo-alcohols 5-7, respectively.

1. Experimental Procedure for the Synthesis of Amino Ketone 1

To a round-bottomed flask containing ketopinic acid (4.8 g, 26.3 mmol) were added acetone (50 mL) and triethylamine (4 mL), followed by stirring at 0° C. Ethyl chloroformate (5 mL, 52.3 mmol) was gradually dropped thereinto and stirred for 20 minutes. Sodium azide (2.5 g, 38.5 mmol) was dissolved in minimum water and added into the flask, followed by stirring for 1 hour under ice-bath condition. Subsequently, the mixture was warmed to room temperature and stirred for 14 hours. After the reaction was accomplished, the mixture was concentrated to remove acetone, and $HCl_{(aq)}$ (1 N) was added into the flask to adjust the pH value to about 7. The mixture was then extracted with ether, and the combined organic solution was dried over $Na_2SO_4$, filtered and concentrated under high vacuum to give the white solid. The resulting solid was disposed in a flask and $HCl_{(aq)}$ (1 N, 50 mL) was added thereto to perform reaction under reflux for 12 hours. After the reaction was accomplished, the flask was cooled to 0° C., and the pH value was adjusted to about 13 with $NaOH_{(aq)}$ (2N). The mixture was then extracted with ethyl acetate, and the combined organic solution was dried over $Na_2SO_4$, filtered and concentrated under high vacuum to obtain the chiral amino ketone 1 (2.58 g, 64%).

2. Experimental Procedure for the Synthesis of Amino Ketones 2-4

Amino ketone 1 (100 mg, 0.65 mmol) and potassium carbonate (200 mg, 1.45 mmol) were added to a 10 mL round-bottomed flask and then the flask was subjected to vacuum conditions. Subsequently, acetonitrile (2.5 mL) and the corresponding dibromide (0.98 mmol) were added thereto in sequence, followed by stirring for 10 minutes. The mixture was heated under reflux for 20 h and then extracted with $CH_2Cl_2$ (5 mL x3). The combined organic solution was dried over $Na_2SO_4$ and concentrated to give the crude product, which was purified via column chromatography (ethyl acetate:n-hexane=1:3) to yield the desired amino ketone 2-4.

2.1. (1S)-7,7-Dimethyl-1-pyrrolidin-1-yl-bicyclo[2.2.1]heptan-2-one 2

$[\alpha]_D^{24}$ =+45.2 (c 1.0, CHCl₃); ¹H NMR (400 MHz, CDCl₃) δ 3.08-3.03 (m, 2H), 2.85-2.81 (m, 2H), 2.41-2.34 (m, 1H), 2.13 (dt, J=12.8, 3.2 Hz, 1H), 2.05-1.98 (m, 1H), 1.91 (t, J=4.6 Hz, 1H), 1.86-1.67 (m, 6H), 1.40-1.33 (m, 1H), 1.08 (s, 3H), 1.06 (s, 3H); ¹³C NMR. (100 MHz, CDCl₃) δ 217.4 (C), 77.0 (C), 48.0 (CH₂), 46.9 (C), 42.8 (CH), 42.6 (CH₂), 27.7 (CH₂), 25.9 (CH₂), 24.1 (CH₂), 22.0 (CH₃), 19.7 (CH₃); IR (neat) 2963 (s), 2876 (m), 1742 (s) cm⁻¹; HRMS calcd for $C_{13}H_{21}NO$ 207.1623. found 207.1620.

2.2. (1S)-7,7-Dimethyl-1-piperidin-1-yl-bicyclo[2.2.1]heptan-2-one 3

$[\alpha]_D^{24}$=+91.4 (c 1.0, CHCl₃); mp 78.0-79.0° C.; ¹H NMR (400 MHz, CDCl₃) δ2.90-2.82 (m, 2H), 2.78-2.70 (m, 2H), 2.42-2.32 (m, 1H), 2.15 (dt, J=12.6, 3.6 Hz, 1H), 2.00-1.90 (m, 1H), 1.88-1.78 (m, 2H), 1.58-1.46 (m, 5H), 1.45-1.39 (m, 2H), 1.36-1.28 (m, 1H), 1.11 (s, 6H); ¹³C NMR (100 MHz, CDCl₃) δ 217.5 (C), 79.2 (C), 49.0 (CH₂), 47.4 (C), 43.6 (CH), 43.0 (CH₂), 26.8 (CH₂), 26.3 (CH₂), 25.7 (CH₂), 24.5 (CH₂), 23.3 (CH₃), 21.1 (CH₃); IR (neat) 2971 (w), 2926 (m), 1739 (s) cm⁻¹, HRMS calcd for $C_{14}H_{23}NO$ 221.1780. found 221.1792.

2.3. (1S)-7,7-Dimethyl-1-morpholin-4-yl-bicyclo[2.2.1]-heptan-2-one 4

$[\alpha]_D^{24}$=+82.5 (c 1.0, CHCl₃); mp 89.5-90.5° C.; ¹H NMR (400 MHz, CDCl₃) δ 3.63 (t, J=4.8 Hz, 4H), 3.00-2.90 (m, 2H), 2.81-2.76 (m, 2H), 2.39-2.33 (m, 1H), 2.08 (dt, J=12.4, 3.6 Hz, 1H), 2.00-1.92 (m, 1H), 1.85-1.80 (m, 2H), 1.57-1.50 (m, 1H), 1.34-1.31 (m, 1H), 1.09 (s, 3H), 1.08 (s, 3H); ¹³C NMR (100 MHz, CDCl₃) δ 217.1 (C), 78.6 (C), 67.7 (CH₂), 48.5 (CH₂), 47.5 (C), 43.8 (CH), 43.1 (CH₂), 26.0 (CH₂), 25.8 (CH₂), 23.3 (CH₃), 21.0 (CH₃); IR (neat) 2958 (s), 2889 (m), 2850 (s), 1743 (s) cm⁻¹; HRMS calcd for $C_{13}H_{21}NO_2$ 223.1572, found 223.1567.

3. Experimental Procedure for the Synthesis of β-Amino Alcohols 5-7

A 25 mL round-bottomed flask containing the chiral amino ketone 2-4 (0.45 mmol), CeCl₃ (0.28 g, 0.11 mmol), and methanol (3 mL) was cooled to −78° C., followed by the addition of NaBH₄ (0.08 g, 2.11 mmol). The flask was slowly warmed to −20° C. After 2 h at −20° C., the flask was slowly warmed to 25° C., and was kept at ambient temperature for 6 h. The solvents were then removed in vacuo, followed by extraction with $CH_2Cl_2$ (15 mL×3). The organic solution was dried over $Na_2SO_4$, filtered and concentrated, to give the crude product, which was purified by column chromatography (ethyl acetate:n-hexane=1:3) to yield the chiral amino alcohol 5-7.

3.1. (1S, bicyclo[2.2.1]-heptan-2-ol 5

$[\alpha]_D^{24}$=+1.2 (c 1.0, $CHCl_3$); $^1$H NMR (400 MHz, $CDCl_3$) δ 3.97 (br, 1H), 3.66 (dd, J=7.8, 3.0 Hz, 1H), 2.67-2.62 (m, 2H), 2.55-2.50 (m, 2H), 1.90-1.85 (m, 1H), 1.81-1.60 (m, 7H), 1.51 (t, J=4.4 Hz, 1H), 1.16-1.06 (m, 1H), 1.10 (s, 3H), 1.03-0.96 (m, 1H), 0.99 (s, 3H); $^{13}$C NMR (100 MHz, $CDCl_3$) δ 75.1 (CH), 70.1 (C), 47.0 ($CH_2$), 46.3 (C), 45.7 (CH), 38.4 ($CH_2$), 26.1 ($CH_2$), 22.9 ($CH_2$), 22.8 ($CH_3$), 20.7 ($CH_2$), 20.1 ($CH_3$); IR (neat) 3422 (br), 2958 (s), 2877 (s), 2821 (m) $cm^{-1}$; HRMS calcd for $C_{13}H_{23}NO$ 209.1780. found 209.1774.

3.2. (1S,2R)-7,7-Dimethyl-1-piperidin-1-yl-bicyclo[2.2.1]-heptan-2-ol 6

$[\alpha]_D^{24}$=+14.2 (c 1.0, $CHCl_3$); mp 88.5-89.5° C.; $^1$H NMR (400 MHz, $CDCl_3$) δ 3.72 (d, J=5.2 Hz, 1H), 2.58 (br, 4H), 1.90-1.70 (m, 3H), 1.68-1.36 (m, 8H), 1.18-0.98 (m, 2H), 1.14 (s, 3H), 1.07 (s, 3H); $^{13}$C NMR (100 MHz, $CDCl_3$) δ 73.6 (CH), 72.8 (C), 48.4 ($CH_2$), 46.7 (CH), 45.9 (C), 37.9 ($CH_2$), 26.7 ($CH_2$), 26.3 ($CH_2$), 24.4 ($CH_2$), 24.0 ($CH_3$), 22.3 ($CH_2$) 20.3 ($CH_3$); IR (neat) 3329 (br), 2958 (s), 2932 (s), 2805 (w) $cm^{-1}$; HRMS calcd for $C_{14}H_{25}NO$ 223.1936. found 223.1945.

3.3. (1S,2R)-7,7-Dimethyl-1-morpholin-4-yl-bicyclo[2.2.1]heptan-2-ol 7

$[\alpha]_D^{24}$=+11.0 (c 1.0, $CHCl_3$); mp 35.0-36.0° C.; $^1$H NMR (400 MHz, $CDCl_3$) δ 3.74-3.66 (m, 5H), 2.67-2.61 (m, 2H), 2.57-2.50 (m, 2H), 1.92-1.76 (m, 3H), 1.69-1.62 (m, 1H), 1.52 (t, J=4.6 Hz, 1H), 1.18-1.00 (m, 2H), 1.14 (s, 3H), 1.06 (s, 3H); $^{13}$C NMR (100 MHz, $CDCl_3$) δ 72.8 (CH), 71.8 (C), 66.7 ($CH_2$), 47.2 ($CH_2$), 46.0 (CH), 45.3 (C), 37.5 ($CH_2$), 25.7 ($CH_2$), 23.3 ($CH_3$), 21.7 ($CH_2$), 19.8 ($CH_3$); IR (neat) 3415 (br), 2956 (s), 2884 (s), 2850 (m) $cm^{-1}$; HRMS calcd for $C_{13}H_{23}NO_2$ 225.1729. found 225.1713; Elemental analysis: calcd: C, 69.29; H, 10.29; N, 6.22. found: C, 69.49; H, 9.39; N, 6.24.

Reaction Example 1

Optimization of the Reaction Conditions with Respect to Enantioselective Addition of Organozinc to Imines Through the following reactions, the effect of various reaction parameters on yield and enantiomeric excess (ee) were examined, and the results were shown in the following tables 1 to 3. Herein, the concentration (M) shown in solvent brackets refers to the concentration of imines in a solvent.

1.1 Solvent Effect

TABLE 1

8a + 7 (1 eq.), $Et_2Zn$ (5 eq.), rt, 24 h → 9a

| Entry | Solvent | Yield$^a$ (%) | ee$^b$ (%) |
|---|---|---|---|
| 1 | n-hexane (0.057M) | >99 | 95 |
| 2$^c$ | n-hexane (0.072M) | 98 | 96 |
| 3 | n-hexane (0.072M) | >99 | 96 |
| 4 | n-hexane (0.11M) | 98 | 95 |
| 5$^c$ | n-hexane (0.2M) | 94 | 95 |
| 6 | n-hexane (0.2M) | 97 | 95 |
| 7 | toluene (0.075M) | 96 | 95 |
| 8$^c$ | toluene (0.22M) | 97 | 95 |
| 9 | toluene (0.22M) | 95 | 96 |
| 10 | toluene:n-hexane (1:1, 0.057M) | 95 | 96 |
| 11$^c$ | toluene:n-hexane (1.76:1, 0.072M) | 94 | 94 |
| 12 | toluene:n-hexane (1.76:1, 0.072M) | 93 | 96 |
| 13 | dichloromethane:n-hexane (1:1, 0.057M) | >99 | 93 |
| 14 | THF:n-hexane (1.76:1, 0.072M) | 97 | 93 |
| 15 | acetonitrile:n-hexane (1.76:1, 0.072M) | 45 | 93 |

$^a$Isolated yield after column chromatography.
$^b$Determination by HPLC on the OD—H chiral column.
$^c$Reaction time being 1 h.

As shown in Table 1, adducts were prepared in high enantioselectivity by using n-hexane, toluene, toluene/n-hexane, dichloromethane/n-hexane, THF/n-hexane or acetonitrile/n-hexane as a solvent.

<1.1.1. Experimental Procedure of Entry 1>

To a 10 mL round-bottomed flask were added imine (0.17 mmol) and amino alcohol 7 (0.038 g, 0.17 mmol) in n-hexane (1.5 mL), followed by the addition of a diethylzinc solution (10 wt % in n-hexane, 1.5 mL, 0.85 mmol) under ice-bath condition. The reaction solution was stirred for 24 hours at room temperature and then an ammonium chloride solution (1 N aqueous solution, 4 mL) was added thereto to stop the reaction. Subsequently, the reaction solution was acidified (pH=2) by $HCl_{(aq)}$ (1 N) and separated into an organic layer and an aqueous layer. The aqueous layer was extracted with dichlormethane (10 mL×3) and the organic layer was dried over $Na_2SO_4$ (anhydrous), filtered and concentrated, to give the crude product, which was purified by column chromatography (methanol:dichlormethane=1:40-1:20 as a eulation) to yield the adduct.

<1.1.2. Experimental Procedure of Entry 2>

To a 10 mL round-bottomed flask were added imine (0.34 mmol) and amino alcohol 7 (0.0766 g, 0.34 mmol) in n-hexane (3 mL), followed by the addition of a diethylzinc solution (1.0 M in n-hexane, 1.7 mL, 1.7 mmol) under ice-bath condition. The reaction solution was stirred for 1 hour at room temperature and then an ammonium chloride solution (1 N aqueous solution, 4 mL) was added thereto to stop the reaction. Subsequently, the reaction solution was acidified (pH=2) by $HCl_{(aq)}$ (1 N) and separated into an organic layer and an aqueous layer. The aqueous layer was extracted with dichlormethane (10 mL×3) and the organic layer was dried over Na₂SO₄ (anhydrous), filtered and concentrated, to give the crude product, which was purified by column chromatography (methanol:dichlormethane=1:40-1:20 as a eulation) to yield the adduct.

<1.1.3. Experimental Procedure of Entry 3>

The experimental procedure of this entry was the same as that illustrated in entry 2, except that the reaction time of this entry was 24 hours.

<1.1.4. Experimental Procedure of Entry 4>

To a 10 mL round-bottomed flask were added imine (0.34 mmol) and amino alcohol 7 (0.0766 g, 0.34 mmol), followed by the addition of a diethylzinc solution (10 wt % in n-hexane, 3 mL, 1.7 mmol) under ice-bath condition. The reaction solution was stirred for 24 hours at room temperature and then an ammonium chloride solution (1 N aqueous solution, 4 mL) was added thereto to stop the reaction. Subsequently, the reaction solution was acidified (pH=2) by $HCl_{(aq)}$ (1 N) and separated into an organic layer and an aqueous layer. The aqueous layer was extracted with dichlormethane (10 mL×3) and the organic layer was dried over Na₂SO₄ (anhydrous), filtered and concentrated, to give the crude product, which was purified by column chromatography (methanol:dichlormethane=1:40-1:20 as a eulation) to yield the adduct.

<1.1.5. Experimental Procedure of Entry 5>

To a 10 mL round-bottomed flask were added imine (0.34 mmol) and amino alcohol 7 (0.0766 g, 0.34 mmol), followed by the addition of a diethylzinc solution (1.0 M in n-hexane, 1.7 mL, 1.7 mmol) under ice-bath condition. The reaction solution was stirred for 1 hour at room temperature and then an ammonium chloride solution (1 N aqueous solution, 4 mL) was added thereto to stop the reaction. Subsequently, the reaction solution was acidified (pH=2) by $HCl_{(aq)}$ (1 N) and separated into an organic layer and an aqueous layer. The aqueous layer was extracted with dichlormethane (10 mL×3) and the organic layer was dried over Na₂SO₄ (anhydrous), filtered and concentrated, to give the crude product, which was purified by column chromatography (methanol:dichlormethane=1:40-1:20 as a eulation) to yield the adduct.

< 1.1.6. Experimental Procedure of Entry 6>

The experimental procedure of this entry was the same as that illustrated in entry 5, except that the reaction time of this entry was 24 hours.

<1.1.7. Experimental Procedure of Entry 7>

To a 10 mL round-bottomed flask were added imine (0.34 mmol) and amino alcohol 7 (0.0766 g, 0.34 mmol) in toluene (3 mL), followed by the addition of a diethylzinc solution (1.1 M in toluene, 1.55 mL, 1.7 mmol) under ice-bath condition. The reaction solution was stirred for 24 hours at room temperature and then an ammonium chloride solution (1 N aqueous solution, 4 mL) was added thereto to stop the reaction. Subsequently, the reaction solution was acidified (pH=2) by $HCl_{(aq)}$ (1 N) and separated into an organic layer and an aqueous layer. The aqueous layer was extracted with dichlormethane (10 mL×3) and the organic layer was dried over Na₂SO₄ (anhydrous), filtered and concentrated, to give the crude product, which was purified by column chromatography (methanol:dichlormethane=1:40-1:20 as a eulation) to yield the adduct.

<1.1.8. Experimental Procedure of Entry 8>

To a 10 mL round-bottomed flask were added imine (0.34 mmol) and amino alcohol 7 (0.0766 g, 0.34 mmol), followed by the addition of a diethylzinc solution (1.1 M in toluene, 1.55 mL, 1.7 mmol) under ice-bath condition. The reaction solution was stirred for 1 hour at room temperature and then an ammonium chloride solution (1 N aqueous solution, 4 mL) was added thereto to stop the reaction. Subsequently, the reaction solution was acidified (pH=2) by $HCl_{(aq)}$ (1 N) and separated into an organic layer and an aqueous layer. The aqueous layer was extracted with dichlormethane (10 mL×3) and the organic layer was dried over Na₂SO₄ (anhydrous), filtered and concentrated, to give the crude product, which was purified by column chromatography (methanol:dichlormethane=1:40-1:20 as a eulation) to yield the adduct.

<1.1.9. Experimental Procedure of Entry 9>

The experimental procedure of this entry was the same as that illustrated in entry 8, except that the reaction time of this entry was 24 hours.

<1.1.10. Experimental Procedure of Entry 10>

The experimental procedure of this entry was the same as that illustrated in entry 1, except that the solvent used in this entry was toluene: n-hexane (1:1).

<1.1.11. Experimental Procedure of Entry 11>

The experimental procedure of this entry was the same as that illustrated in entry 2, except that the solvent used in this entry was toluene:n-hexane (1.76:1).

<1.1.12. Experimental Procedure of Entry 12>

The experimental procedure of this entry was the same as that illustrated in entry 3, except that the solvent used in this entry was toluene:n-hexane (1.76:1).

<1.1.13. Experimental Procedure of Entry 13>

The experimental procedure of this entry was the same as that illustrated in entry 1, except that the solvent used in this entry was dichloromethane:n-hexane (1:1).

<1.1.14. Experimental Procedure of Entry 14>

The experimental procedure of this entry was the same as that illustrated in entry 3, except that the solvent used in this entry was THF:n-hexane (1.76:1).

<1.1.15. Experimental Procedure of Entry 15>

The experimental procedure of this entry was the same as that illustrated in entry 3, except that the solvent used in this entry was acetonitrile:n-hexane (1.76:1).

1.2. Amount Effect of β-Amino Alcohol 7 and Diethylzinc

TABLE 2

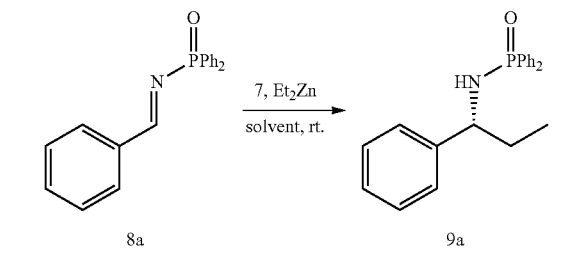

| Entry | Amount of 7 (equivents) | Amnout of diethylzinc (equivents) | Solvent | Time (hours) | Yield[a] (%) | ee[b] (%) |
|---|---|---|---|---|---|---|
| 1 | 1 | 5 | toluene (0.22M) | 1 | 97 | 95 |
| 2 | 0.6 | 5 | toluene (0.22M) | 25 | 88 | 92 |
| 3 | 0.6 | 3 | toluene (0.365M) | 28.5 | 88 | 88 |
| 4 | 0.6 | 2 | toluene (0.55M) | 28.5 | 92 | 85 |
| 5 | 0.5 | 6 | toluene (0.18M) | 25 | 79 | 92 |
| 6 | 0.5 | 5 | toluene (0.22M) | 25 | 76 | 89 |
| 7 | 0.5 | 4 | toluene (0.275M) | 25 | 80 | 86 |
| 8 | 0.4 | 6 | toluene (0.18M) | 25 | 72 | 84 |
| 9 | 0.4 | 5 | toluene (0.22M) | 25 | 69 | 84 |

TABLE 2-continued

8a → 9a (7, Et₂Zn, solvent, rt.)

| Entry | Amount of 7 (equivents) | Amnout of diethylzinc (equivents) | Solvent | Time (hours) | Yield[a] (%) | ee[b] (%) |
|---|---|---|---|---|---|---|
| 10 | 0.25 | 5 | toluene (0.22M) | 35 | 53 | 74 |
| 11[c] | 1 | 5 | toluene:n-hexane (1.76:1, 0.072M) | 1 | 94 | 94 |
| 12[c] | 0.6 | 5 | toluene:n-hexane (1.76:1, 0.072M) | 48 | 87 | 93 |
| 13[c] | 0.6 | 4 | toluene:n-hexane (2.2:1, 0.078M) | 48 | 90 | 93 |
| 14[c] | 0.6 | 3 | toluene:n-hexane (3:1, 0.085M) | 42 | 93 | 92 |
| 15[c] | 0.5 | 5 | toluene:n-hexane (1.76:1, 0.072M) | 48 | 82 | 91 |
| 16[c] | 0.5 | 4 | toluene:n-hexane (2.2:1, 0.078M) | 48 | 82 | 90 |
| 17[c] | 0.5 | 3 | toluene:n-hexane (3:1, 0.085M) | 48 | 88 | 88 |
| 18[c] | 0.5 | 2 | toluene:n-hexane (4.41:1, 0.092M) | 48 | 89 | 85 |
| 19[c] | 0.4 | 5 | toluene:n-hexane (1.76:1, 0.072M) | 82 | 82 | 85 |

[a] Isolated yield after column chromatography.
[b] Determination by HPLC on the OD—H chiral column.
[c] Reaction being performed in a mixture of toluene of n-hexane.

As shown in Table 2, high enantioselectivity was maintained while the amount of β-amino alcohol 7 was decreased from 1 equivalent to 0.6 equivalent. However, enantioselectivity was decreased to 85% (ee) and 84% (ee) in the case of further decreasing the amount of β-amino alcohol 7 to 0.4 equivalent. Additionally, high enantioselectivity was maintained while the amount of organozinc was decreased from 6 equivalents to 3 equivalents. However, enantioselectivity was decreased to 85% (ee) in the case of further decreasing the amount of organozinc to 2 equivalents.

<1.2.1. Experimental Procedure of Entry 1>

To a 10 mL round-bottomed flask were added imine (0.34 mmol) and amino alcohol 7 (0.0766 g, 0.34 mmol), followed by the addition of a diethylzinc solution (1.1 M in toluene, 1.55 mL, 1.7 mmol) under ice-bath condition. The reaction solution was stirred for 1 hour at room temperature and then an ammonium chloride solution (1 N aqueous solution, 4 mL) was added thereto to stop the reaction. Subsequently, the reaction solution was acidified (pH=2) by $HCl_{(aq)}$ (1 N) and separated into an organic layer and an aqueous layer. The aqueous layer was extracted with dichlormethane (10 mL×3) and the organic layer was dried over $Na_2SO_4$ (anhydrous), filtered and concentrated, to give the crude product, which was purified by column chromatography (methanol:dichlormethane=1:40-1:20 as a eulation) to yield the adduct.

<1.2.2. Experimental Procedure of Entry 2>

To a 10 mL round-bottomed flask were added imine (0.34 mmol) and amino alcohol 7 (0.046 g, 0.204 mmol), followed by the addition of a diethylzinc solution (1.1 M in toluene, 1.55 mL, 1.7 mmol) under ice-bath condition. The reaction solution was stirred for 25 hours at room temperature and then an ammonium chloride solution (1 N aqueous solution, 4 mL) was added thereto to stop the reaction. Subsequently, the reaction solution was acidified (pH=2) by $HCl_{(aq)}$ (1 N) and separated into an organic layer and an aqueous layer. The aqueous layer was extracted with dichlormethane (10 mL×3) and the organic layer was dried over $Na_2SO_4$ (anhydrous), filtered and concentrated, to give the crude product, which was purified by column chromatography (methanol:dichlormethane=1:40-1:20 as a eulation) to yield the adduct.

<1.2.3. Experimental Procedure of Entry 3>

To a 10 mL round-bottomed flask were added imine (0.34 mmol) and amino alcohol 7 (0.046 g, 0.204 mmol), followed by the addition of a diethylzinc solution (1.1 M in toluene, 0.93 mL, 1.02 mmol) under ice-bath condition. The reaction solution was stirred for 28.5 hours at room temperature and then an ammonium chloride solution (1 N aqueous solution, 4 mL) was added thereto to stop the reaction. Subsequently, the reaction solution was acidified (pH=2) by $HCl_{(aq)}$ (1 N) and separated into an organic layer and an aqueous layer. The aqueous layer was extracted with dichlormethane (10 mL×3) and the organic layer was dried over $Na_2SO_4$ (anhydrous), filtered and concentrated, to give the crude product, which was purified by column chromatography (methanol:dichlormethane=1:40-1:20 as a eulation) to yield the adduct.

<1.2.4. Experimental Procedure of Entry 4>

To a 10 mL round-bottomed flask were added imine (0.34 mmol) and amino alcohol 7 (0.046 g, 0.204 mmol), followed by the addition of a diethylzinc solution (1.1 M in toluene, 0.62 mL, 0.68 mmol) under ice-bath condition. The reaction solution was stirred for 28.5 hours at room temperature and then an ammonium chloride solution (1 N aqueous solution, 4 mL) was added thereto to stop the reaction. Subsequently, the reaction solution was acidified (pH=2) by $HCl_{(aq)}$ (1 N) and separated into an organic layer and an aqueous layer. The aqueous layer was extracted with dichlormethane (10 mL×3) and the organic layer was dried over $Na_2SO_4$ (anhydrous), filtered and concentrated, to give the crude product, which was purified by column chromatography (methanol:dichlormethane=1:40-1:20 as a eulation) to yield the adduct.

<1.2.5. Experimental Procedure of Entry 5>

To a 10 mL round-bottomed flask were added imine (0.34 mmol) and amino alcohol 7 (0.038 g, 0.17 mmol), followed by the addition of a diethylzinc solution (1.1 M in toluene, 1.85 mL, 2.04 mmol) under ice-bath condition. The reaction solution was stirred for 25 hours at room temperature and then an ammonium chloride solution (1 N aqueous solution, 4 mL) was added thereto to stop the reaction. Subsequently, the reaction solution was acidified (pH=2) by $HCl_{(aq)}$ (1 N) and separated into an organic layer and an aqueous layer. The aqueous layer was extracted with dichlormethane (10 mL×3) and the organic layer was dried over $Na_2SO_4$ (anhydrous), filtered and concentrated, to give the crude product, which was purified by column chromatography (methanol:dichlormethane=1:40-1:20 as a eulation) to yield the adduct.

<1.2.6. Experimental Procedure of Entry 6>

To a 10 mL round-bottomed flask were added imine (0.34 mmol) and amino alcohol 7 (0.038 g, 0.17 mmol), followed by the addition of a diethylzinc solution (1.1 M in toluene, 1.55 mL, 1.7 mmol) under ice-bath condition. The reaction solution was stirred for 25 hours at room temperature and then an ammonium chloride solution (1 N aqueous solution, 4 mL) was added thereto to stop the reaction. Subsequently, the reaction solution was acidified (pH=2) by $HCl_{(aq)}$ (1 N) and separated into an organic layer and an aqueous layer. The aqueous layer was extracted with dichlormethane (10 mL×3) and the organic layer was dried over $Na_2SO_4$ (anhydrous), filtered and concentrated, to give the crude product, which was purified by column chromatography (methanol:dichlormethane=1:40-1:20 as a eulation) to yield the adduct.

<1.2.7. Experimental Procedure of Entry 7>

To a 10 mL round-bottomed flask were added imine (0.34 mmol) and amino alcohol 7 (0.038 g, 0.17 mmol), followed by the addition of a diethylzinc solution (1.1 M in toluene, 1.24 mL, 1.36 mmol) under ice-bath condition. The reaction solution was stirred for 25 hours at room temperature and then an ammonium chloride solution (1 N aqueous solution, 4 mL) was added thereto to stop the reaction. Subsequently, the reaction solution was acidified (pH=2) by $HCl_{(aq)}$ (1 N) and separated into an organic layer and an aqueous layer. The aqueous layer was extracted with dichlormethane (10 mL×3) and the organic layer was dried over $Na_2SO_4$ (anhydrous), filtered and concentrated, to give the crude product, which was purified by column chromatography (methanol:dichlormethane=1:40-1:20 as a eulation) to yield the adduct.

<1.2.8. Experimental Procedure of Entry 8>

To a 10 mL round-bottomed flask were added imine (0.34 mmol) and amino alcohol 7 (0.030 g, 0.136 mmol), followed by the addition of a diethylzinc solution (1.1 M in toluene, 1.85 mL, 2.04 mmol) under ice-bath condition. The reaction solution was stirred for 25 hours at room temperature and then an ammonium chloride solution (1 N aqueous solution, 4 mL) was added thereto to stop the reaction. Subsequently, the reaction solution was acidified (pH=2) by $HCl_{(aq)}$ (1 N) and separated into an organic layer and an aqueous layer. The aqueous layer was extracted with dichlormethane (10 mL×3) and the organic layer was dried over $Na_2SO_4$ (anhydrous), filtered and concentrated, to give the crude product, which was purified by column chromatography (methanol:dichlormethane=1:40-1:20 as a eulation) to yield the adduct.

<1.2.9. Experimental Procedure of Entry 9>

To a 10 mL round-bottomed flask were added imine (0.34 mmol) and amino alcohol 7 (0.030 g, 0.136 mmol), followed by the addition of a diethylzinc solution (1.1 M in toluene, 1.55 mL, 1.7 mmol) under ice-bath condition. The reaction solution was stirred for 25 hours at room temperature and then an ammonium chloride solution (1 N aqueous solution, 4 mL) was added thereto to stop the reaction. Subsequently, the reaction solution was acidified (pH=2) by $HCl_{(aq)}$ (1 N) and separated into an organic layer and an aqueous layer. The aqueous layer was extracted with dichlormethane (10 mL×3) and the organic layer was dried over $Na_2SO_4$ (anhydrous), filtered and concentrated, to give the crude product, which was purified by column chromatography (methanol:dichlormethane=1:40-1:20 as a eulation) to yield the adduct.

<1.2.10. Experimental Procedure of Entry 10>

To a 10 mL round-bottomed flask were added imine (0.34 mmol) and amino alcohol 7 (0.019 g, 0.085 mmol), followed by the addition of a diethylzinc solution (1.1 M in toluene, 1.55 mL, 1.7 mmol) under ice-bath condition. The reaction solution was stirred for 35 hours at room temperature and then an ammonium chloride solution (1 N aqueous solution, 4 mL) was added thereto to stop the reaction. Subsequently, the reaction solution was acidified (pH=2) by $HCl_{(aq)}$ (1 N) and separated into an organic layer and an aqueous layer. The aqueous layer was extracted with dichlormethane (10 mL×3) and the organic layer was dried over $Na_2SO_4$ (anhydrous), filtered and concentrated, to give the crude product, which was purified by column chromatography (methanol:dichlormethane=1:40-1:20 as a eulation) to yield the adduct.

<1.2.11. Experimental Procedure of Entry 11>

To a 10 mL round-bottomed flask were added imine (0.34 mmol) and amino alcohol 7 (0.0766 g, 0.34 mmol) in toluene (3 mL), followed by the addition of a diethylzinc solution (1.0 M in n-hexane, 1.7 mL, 1.7 mmol) under ice-bath condition. The reaction solution was stirred for 1 hour at room temperature and then an ammonium chloride solution (1 N aqueous solution, 4 mL) was added thereto to stop the reaction. Subsequently, the reaction solution was acidified (pH=2) by $HCl_{(aq)}$ (1 N) and separated into an organic layer and an aqueous layer. The aqueous layer was extracted with dichlormethane (10 mL×3) and the organic layer was dried over $Na_2SO_4$ (anhydrous), filtered and concentrated, to give the crude product, which was purified by column chromatography (methanol:dichlormethane=1:40-1:20 as a eulation) to yield the adduct.

<1.1.12. Experimental Procedure of Entry 12>

The experimental procedure of this entry was the same as that illustrated in entry 11, except that the amount of amino alcohol 7 used in this entry was 0.046 g (0.204 mmol) and the reaction time of this entry was 48 hours.

<1.2.13. Experimental Procedure of Entry 13>

To a 10 mL round-bottomed flask were added imine (0.34 mmol) and amino alcohol 7 (0.046 g, 0.204 mmol) in toluene (3 mL), followed by the addition of a diethylzinc solution (1.0 M in n-hexane, 1.36 mL, 1.36 mmol) under ice-bath condition. The reaction solution was stirred for 48 hours at room temperature and then an ammonium chloride solution (1 N aqueous solution, 4 mL) was added thereto to stop the reaction. Subsequently, the reaction solution was acidified (pH=2) by $HCl_{(aq)}$ (1 N) and separated into an organic layer and an aqueous layer. The aqueous layer was extracted with dichlormethane (10 mL×3) and the organic layer was dried over $Na_2SO_4$ (anhydrous), filtered and concentrated, to give the crude product, which was purified by column chromatography (methanol:dichlormethane=1:40-1:20 as a eulation) to yield the adduct.

<1.2.14. Experimental Procedure of Entry 14>

To a 10 mL round-bottomed flask were added imine (0.34 mmol) and amino alcohol 7 (0.046 g, 0.204 mmol) in toluene (3 mL), followed by the addition of a diethylzinc solution (1.0 M in n-hexane, 1.02 mL, 1.02 mmol) under ice-bath condition. The reaction solution was stirred for 42 hours at room temperature and then an ammonium chloride solution (1 N aqueous solution, 4 mL) was added thereto to stop the reaction. Subsequently, the reaction solution was acidified (pH=2) by $HCl_{(aq)}$ (1 N) and separated into an organic layer and an aqueous layer. The aqueous layer was extracted with dichlormethane (10 mL×3) and the organic layer was dried over $Na_2SO_4$ (anhydrous), filtered and concentrated, to give the crude product, which was purified by column chromatography (methanol:dichlormethane=1:40-1:20 as a eulation) to yield the adduct.

<1.2.15. Experimental Procedure of Entry 15>

The experimental procedure of this entry was the same as that illustrated in entry 11, except that the amount of amino alcohol 7 used in this entry was 0.038 g (0.17 mmol) and the reaction time of this entry was 48 hours.

<1.2.16. Experimental Procedure of Entry 16>

The experimental procedure of this entry was the same as that illustrated in entry 13, except that the amount of amino alcohol 7 used in this entry was 0.038 g (0.17 mmol).

<1.2.17. Experimental Procedure of Entry 17>

The experimental procedure of this entry was the same as that illustrated in entry 14, except that the amount of amino alcohol 7 used in this entry was 0.038 g (0.17 mmol) and the reaction time of this entry was 48 hours.

<1.2.18. Experimental Procedure of Entry 18>

To a 10 mL round-bottomed flask were added imine (0.34 mmol) and amino alcohol 7 (0.038 g, 0.17 mmol) in toluene (3 mL), followed by the addition of a diethylzinc solution (1.0 M in n-hexane, 0.68 mL, 0.68 mmol) under ice-bath condition. The reaction solution was stirred for 48 hours at room temperature and then an ammonium chloride solution (1 N aqueous solution, 4 mL) was added thereto to stop the reaction. Subsequently, the reaction solution was acidified (pH=2) by $HCl_{(aq)}$ (1 N) and separated into an organic layer and an aqueous layer. The aqueous layer was extracted with dichlormethane (10 mL×3) and the organic layer was dried over $Na_2SO_4$ (anhydrous), filtered and concentrated, to give the crude product, which was purified by column chromatography (methanol:dichlormethane=1:40-1:20 as a eulation) to yield the adduct.

<1.2.19. Experimental Procedure of Entry 19>

The experimental procedure of this entry was the same as that illustrated in entry 11, except that the amount of amino alcohol 7 used in this entry was 0.030 g (0.136 mmol) and the reaction time of this entry was 82 hours.

1.3. Temperature Effect

TABLE 3

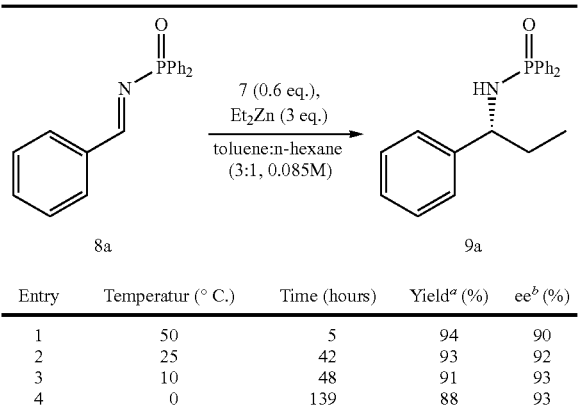

| Entry | Temperatur (° C.) | Time (hours) | Yield[a] (%) | ee[b] (%) |
|---|---|---|---|---|
| 1 | 50 | 5 | 94 | 90 |
| 2 | 25 | 42 | 93 | 92 |
| 3 | 10 | 48 | 91 | 93 |
| 4 | 0 | 139 | 88 | 93 |

[a]Isolated yield after column chromatography.
[b]Determination by HPLC on the OD—H chiral column.

As shown in Table 3, enantioselectivity was enhanced to 93% (ee) by reducing the temperature from room temperature to 10° C.

<1.3.1. Experimental Procedure of Entry 1>

To a 10 mL round-bottomed flask were added imine (0.34 mmol) and amino alcohol 7 (0.046 g, 0.204 mmol) in toluene (3 mL), followed by the addition of a diethylzinc solution (1.0 M in n-hexane, 1.02 mL, 1.02 mmol) under ice-bath condition. The reaction solution was stirred for 5 hours at 50° C. and then an ammonium chloride solution (1 N aqueous solution, 4 mL) was added thereto to stop the reaction. Subsequently, the reaction solution was acidified (pH=2) by $HCl_{(aq)}$ (1 N) and separated into an organic layer and an aqueous layer. The aqueous layer was extracted with dichlormethane (10 mL×3) and the organic layer was dried over $Na_2SO_4$ (anhydrous), filtered and concentrated, to give the crude product, which was purified by column chromatography (methanol:dichlormethane=1:40-1:20 as a eulation) to yield the adduct.

<1.3.2. Experimental Procedure of Entry 2>

The experimental procedure of this entry was the same as that illustrated in entry 1, except that the temperature of this entry was 25° C. and the reaction time of this entry was 42 hours.

<1.3.3. Experimental Procedure of Entry 3>

The experimental procedure of this entry was the same as that illustrated in entry 1, except that the temperature of this entry was 10° C. and the reaction time of this entry was 48 hours.

<1.3.4. Experimental Procedure of Entry 4>

The experimental procedure of this entry was the same as that illustrated in entry 1, except that the temperature of this entry was 0° C. and the reaction time of this entry was 139 hours.

Reaction Example 2

Asymmetric Addition of Various Organozincs to Imine

TABLE 4

| Entry | R' | Solvent | Time (hours) | Yield[a] (%) | ee[b] (%) |
|---|---|---|---|---|---|
| 1 | ethyl | toluene:n-hexane (3:1, 0.085M) | 42 | 93 | 92 |
| 2 | methyl | toluene:n-hexane (2.26:1,0.079M) | 168 | 70 | 96 |
| 3[c] | methyl | toluene:n-hexane (1.36:1,0.065M) | 24 | 86 | 97 |

[a]Isolated yield after column chromatography.
[b]Determination by HPLC on the OD—H chiral column.
[c]7 (1 equivalent) and $Me_2Zn$ (5 equivalents) being used.

As shown in Table 4, high enantioselectivity can be obtained in asymmetric addition of dimethylzinc or diethylzinc to imine.

<2.1. Experimental Procedure of Entry 1>

To a 10 mL round-bottomed flask were added imine (0.34 mmol) and amino alcohol 7 (0.046 g, 0.204 mmol) in toluene (3 mL), followed by the addition of a diethylzinc solution (1.0 M in n-hexane, 1.02 mL, 1.02 mmol) under ice-bath condition. The reaction solution was stirred for 42 hours at room temperature and then an ammonium chloride solution (1 N aqueous solution, 4 mL) was added thereto to stop the reaction. Subsequently, the reaction solution was acidified (pH=2) by $HCl_{(aq)}$ (1 N) and separated into an organic layer and an aqueous layer. The aqueous layer was extracted with dichlormethane (10 mL×3) and the organic layer was dried over $Na_2SO_4$ (anhydrous), filtered and concentrated, to give the crude product, which was purified by column chromatography (methanol:dichlormethane=1:40-1:20 as a eulation) to yield the adduct.

<2.2. Experimental Procedure of Entry 2>

To a 10 mL round-bottomed flask were added imine (0.34 mmol) and amino alcohol 7 (0.046 g, 0.204 mmol) in toluene (3 mL), followed by the addition of a diethylzinc solution (10 wt % in n-hexane, 1.33 mL, 1.02 mmol) under ice-bath condition. The reaction solution was stirred for 168 hours at room temperature and then an ammonium chloride solution (1 N aqueous solution, 4 mL) was added thereto to stop the reaction. Subsequently, the reaction solution was acidified (pH=2) by $HCl_{(aq)}$ (1 N) and separated into an organic layer and an aqueous layer. The aqueous layer was extracted with dichlormethane (10 mL×3) and the organic layer was dried over $Na_2SO_4$ (anhydrous), filtered and concentrated, to give the crude product, which was purified by column chromatography (methanol:dichlormethane=1:40-1:20 as a eulation) to yield the adduct.

<2.3. Experimental Procedure of Entry 3>

To a 10 mL round-bottomed flask were added imine (0.34 mmol) and amino alcohol 7 (0.0766 g, 0.34 mmol) in toluene (3 mL), followed by the addition of a diethylzinc solution (10 wt % in n-hexane, 2.2 mL, 1.7 mmol) under ice-bath condition. The reaction solution was stirred for 24 hours at room temperature and then an ammonium chloride solution (1 N aqueous solution, 4 mL) was added thereto to stop the reaction. Subsequently, the reaction solution was acidified (pH=2) by $HCl_{(aq)}$ (1 N) and separated into an organic layer and an aqueous layer. The aqueous layer was extracted with dichlormethane (10 mL×3) and the organic layer was dried over $Na_2SO_4$ (anhydrous), filtered and concentrated, to give the crude product, which was purified by column chromatography (methanol:dichlormethane=1:40-1:20 as a eulation) to yield the adduct.

Reaction Example 3

Asymmetric Addition of Organozinc to Various Imines

TABLE 5

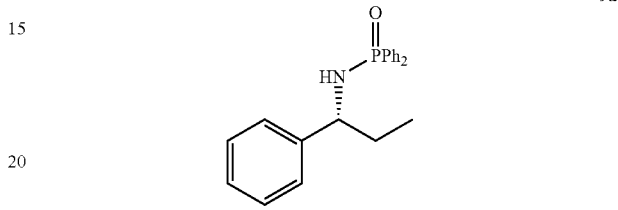

| Entry | Method[c] | R | | Time (hours) | Yield[a] (%) | ee[b] (%) |
|---|---|---|---|---|---|---|
| 1 | A | phenyl | 8a | 42 | 93 | 92 |
| 2 | A | 2-methylphenyl | 8b | 51 | 90 | 89 |
| 3 | A | 3-methylphenyl | 8c | 51 | 93 | 93 |
| 4 | A | 4-methylphenyl | 8d | 51 | 95 | 93 |
| 5 | A | 2-methoxyphenyl | 8e | 25 | 97 | 92 |
| 6 | A | 3-methylphenyl | 8f | 25 | 87 | 93 |
| 7 | A | 4-methylphenyl | 8g | 25 | 88 | 98 |
| 8 | A | 2-chlorophenyl | 8h | 25 | 92 | 85 |
| 9 | A | 3-chlorophenyl | 8i | 30 | 84 | 87 |
| 10 | A | 4-chlorophenyl | 8j | 25 | 92 | 90 |
| 11 | A | 4-methoxycarbonylphenyl | 8k | 25 | 97 | 87 |
| 12 | A | 2-(1-phenylacryl) | 8l | 120 | 33 | 86 |
| 13 | B | 2-(1-phenylacryl) | 8l | 144 | 35 | 94 |
| 14 | C | phenyl | 8a' | 24 | 86 | 97 |
| 15 | C | 4-methylphenyl | 8d' | 24 | 85 | 97 |
| 16 | C | 4-methoxyphenyl | 8g' | 24 | 86 | 98 |
| 17 | C | 4-methoxycarbonylphenyl | 8k' | 24 | 86 | 97 |

[a]Isolated yield after column chromatography.
[b]Determination by HPLC on the OD—H chiral column.
[c]Method A: reaction being performed by using 7 (0.6 equivalent) and Et₂Zn (3 equivalents) in toluene:n-hexane (1.76:1, 0.072M); Method B: reaction being performed by using 7 (1 equivalent) and Et₂Zn (5 equivalents) in toluene:n-hexane (1.76: 1, 0.072M); Method C: reaction being performed by using 7 (1 equivalent) and Me₂Zn (5 equivalents) in toluene: n-hexane (1.36: 1, 0.065M).

As shown in Table 5, high enantioselectivity can be obtained in asymmetric addition of organozinc to various imines.

<3.1. Experimental Procedure of Entry 1>

To a 10 mL round-bottomed flask were added imine 8a (0.34 mmol) and amino alcohol 7 (0.046 g, 0.204 mmol) in toluene (3 mL), followed by the addition of a diethylzinc solution (1.0 M in n-hexane, 1.02 mL, 1.02 mmol) under ice-bath condition. The reaction solution was stirred for 42 hours at room temperature and then an ammonium chloride solution (1 N aqueous solution, 4 mL) was added thereto to stop the reaction. Subsequently, the reaction solution was acidified (pH=2) by $HCl_{(aq)}$ (1 N) and separated into an organic layer and an aqueous layer. The aqueous layer was extracted with dichlormethane (10 mL×3) and the organic layer was dried over $Na_2SO_4$ (anhydrous), filtered and concentrated, to give the crude product, which was purified by column chromatography (methanol:dichlormethane=1:40-1:20 as a eulation) to yield the adduct 9a.

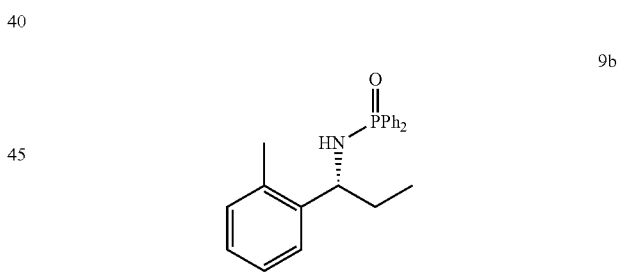

9a $^1$H NMR (400 MHz, CDCl₃) δ 7.86-7.81 (m, 2H), 7.74-7.69 (m, 2H), 7.46-7.36 (m, 4H), 7.31-7.18 (m, 5H), 7.12 (d, J=7.2 Hz, 2H), 4.10-4.02 (m, 1H), 3.28-3.24 (m, 1H), 2.01-1.92 (m, 1H), 1.85-1.75 (m, 1H), 0.76 (t, J=7.2 Hz, 3H); $^{13}$C NMR (100 MHz, CDCl₃) δ 143.45 (d, J=5.1 Hz, C), 132.55, 132.45, 131.78, 131.69, 131.59, 128.42, 128.37, 128.29, 128.24, 128.12, 126.97, 126.44, 57.05 (CH), 32.44 (d, J=3.7 Hz, CH₂), 10.5 (CH₃).

<3.2. Experimental Procedure of Entry 2>

The experimental procedure of this entry was the same as that illustrated in entry 1, except that the imines 8b was used in this entry as a reactant and the reaction time of this entry was 51 hours to yield the adduct 9b.

9b $^1$H NMR (400 MHz, CDCl₃) δ 7.86-7.81 (m, 2H), 7.68-7.63 (m, 2H), 7.45-7.19 (m, 8H), 7.09 (t, J=7.2 Hz, 1H), 6.97-6.96 (m, 1H), 4.35-4.26 (m, 1H), 3.37-3.32 (m, 1H), 1.93-1.88 (m, 1H), 1.85 (s, 3H), 1.8-1.69 (m, 1H), 0.81 (t, J=7.2 Hz, 3H); $^{13}$C NMR (100 MHz, CDCl₃) δ 142.36 (d, J=5.1 Hz, C), 134.72 (C), 132.55, 132.46, 131.75, 131.67, 131.52, 131.15, 130.07, 128.42, 128.30, 128.16, 128.03, 126.57, 126.28, 125.18, 52.29 (CH), 32.64 (CH₂), 18.9 (CH₃), 10.44 (CH₃).

<3.3. Experimental Procedure of Entry 3>

The experimental procedure of this entry was the same as that illustrated in entry 1, except that the imines 8c was used in this entry as a reactant and the reaction time of this entry was 51 hours to yield the adduct 9c.

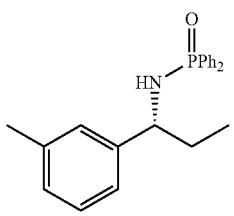

9c

¹H NMR (400 MHz, CDCl₃) δ 7.85-7.8 (m, 2H), 7.75-7.7 (m, 2H), 7.46-7.35 (m, 4H), 7.32-7.27 (m, 2H), 7.15 (t, J=7.6 Hz, 1H), 7.02-7.0 (m, 1H), 6.95-6.93 (m, 1H), 6.88 (s, 1H), 4.03-4.0 (m, 1H), 3.27-3.26 (m, 1H), 2.27 (s, 3H), 2.0-1.94 (m, 1H), 1.83-1.76 (m, 1H), 0.74 (t, J=7.6 Hz, 3H); ¹³C NMR (100 MHz, CDCl₃) δ 143.3 (d, J=5.8 Hz, C), 137.87 (C), 133.93, 132.58, 132.49, 131.76, 131.67, 131.54, 131.35, 128.39, 128.26, 128.19, 128.07, 127.75, 127.27, 123.42, 57.09 (CH), 32.34 (d, J=2.9 Hz, CH₂), 21.38 (CH₃), 10.56 (CH₃).

<3.4. Experimental Procedure of Entry 4>

The experimental procedure of this entry was the same as that illustrated in entry 1, except that the imines 8d was used in this entry as a reactant and the reaction time of this entry was 51 hours to yield the adduct 9d.

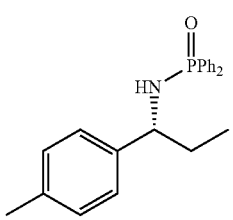

9d

¹H NMR (400 MHz, CDCl₃) δ 7.85-7.8 (m, 2H), 7.75-7.70 (m, 2H), 7.42-7.32 (m, 4H), 7.30-7.25 (m, 2H), 7.07-7.01 (m, 4H), 4.05-3.97 (m, 1H), 3.31-3.29 (m, 1H), 2.28 (s, 3H), 2.02-1.92 (m, 1H), 1.84-1.73 (m, 1H), 0.74 (t, J=7.2 Hz, 3H); ¹³C NMR (100 MHz, CDCl₃) δ 140.39 (d, J=5.9 Hz, C), 136.40, 132.63, 132.46, 132.37, 131.72, 131.54, 131.44, 128.95, 128.29, 128.16, 128.02, 126.27, 56.78 (CH), 32.31 (d, J=3 Hz, CH₂), 20.91 (CH₃), 10.48 (CH₃).

<3.5. Experimental Procedure of Entry 5>

The experimental procedure of this entry was the same as that illustrated in entry 1, except that the imines 8e was used in this entry as a reactant and the reaction time of this entry was 25 hours to yield the adduct 9e.

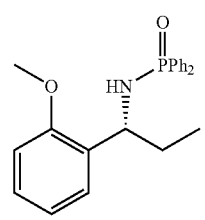

9e

¹H NMR (400 MHz, CDCl₃) δ 7.84-7.79 (m, 2H), 7.74-7.68 (m, 2H), 7.43-7.34 (m, 4H), 7.13-7.26 (m, 2H), 7.21-7.17 (m, 1H), 6.93-6.91 (m, 1H), 6.86-6.81 (m, 2H), 4.16-4.07 (m, 1H), 4.0-3.95 (m, 1H), 3.7 (s, 3H), 2.01-1.93 (m, 1H), 1.92-1.83 (m, 1H), 0.74 (t, J=7.2 Hz, 3H); ¹³C NMR (100 MHz, CDCl₃) δ 156.92, 132.93, 132.64, 132.55, 131.78, 131.68, 131.56, 131.43, 128.51, 128.38, 128.26, 128.15, 128.03, 120.50, 110.93, 55.4 (CH₃), 55.13 (CH), 30.94 (d, J=3.7 Hz, CH₂), 11.13 (CH₃).

<3.6. Experimental Procedure of Entry 6>

The experimental procedure of this entry was the same as that illustrated in entry 1, except that the imines 8f was used in this entry as a reactant and the reaction time of this entry was 25 hours to yield the adduct 9f.

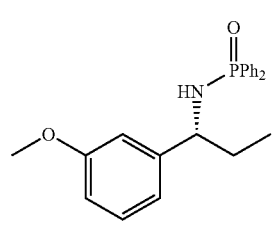

9f

¹H NMR (400 MHz, CDCl₃) δ 7.84-7.79 (m, 2H), 7.74-7.69 (m, 2H), 7.44-7.34 (m, 4H), 7.30-7.26 (m, 2H), 7.17 (t, J=8 Hz, 1H), 6.74-6.71 (m, 2H), 6.65 (t, J=2 Hz, 1H), 4.06-3.98 (m, 1H), 3.71 (s, 3H), 3.34-3.3 (m, 1H), 1.99-1.9 (m, 1H), 1.84-1.73 (m, 1H), 0.75 (t, J=7.2 Hz, 3H); ¹³C NMR (100 MHz, CDCl₃) δ 159.51 (C), 145.12 (d, J=5.1 Hz, C), 133.83, 132.54, 132.44, 131.74, 131.64, 131.56, 131.29, 129.38, 128.39, 128.26, 128.20, 128.07, 118.73, 112.39, 112.09, 57.02 (CH), 55.05 (CH₃), 32.29 (d, J=3 Hz, CH₂), 10.49 (CH₃).

<3.7. Experimental Procedure of Entry 7>

The experimental procedure of this entry was the same as that illustrated in entry 1, except that the imines 8g was used in this entry as a reactant and the reaction time of this entry was 25 hours to yield the adduct 9g.

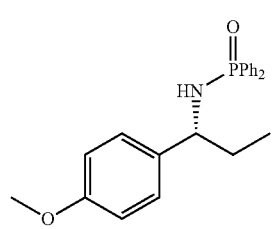

9g

¹H NMR (400 MHz, CDCl₃) δ 7.85-7.8 (m, 2H), 7.75-7.7 (m, 2H), 7.45-7.36 (m, 4H), 7.32-7.27 (m, 2H), 7.04 (d, J=8.8 Hz, 2H), 6.79 (d, J=8.4 Hz, 2H), 4.05-3.95 (m, 1H), 3.75 (s, 3H), 3.25-3.21 (m, 1H), 1.99-1.91 (m, 1H), 1.8-1.73 (m, 1H), 0.73 (t, J=7.2 Hz, 3H); ¹³C NMR (100 MHz, CDCl₃) δ 158.46 (C), 135.59 (d, J=5.9 Hz, C), 132.52, 132.43, 131.78, 131.69, 131.54, 128.4, 128.28, 128.12, 127.55, 113.7, 56.54 (CH), 55.15 (CH₃), 32.38 (CH₂), 10.57 (CH₃).

<3.8. Experimental Procedure of Entry 8>

The experimental procedure of this entry was the same as that illustrated in entry 1, except that the imines 8h was used in this entry as a reactant and the reaction time of this entry was 25 hours to yield the adduct 9h.

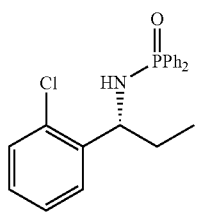

9h

¹H NMR (400 MHz, CDCl₃) δ 7.83-7.78 (m, 2H), 7.69-7.63 (m, 2H), 7.43-7.32 (m, 4H), 7.27-7.16 (m, 5H), 7.12-7.07 (m, 1H), 4.49-4.41 (m, 1H), 3.74-3.70 (m, 1H), 1.94-1.80 (m, 2H), 0.82 (t, J=7.2 Hz, 3H); ¹³C NMR (100 MHz, CDCl₃) δ 140.96 (d, J=4.4 Hz, C), 133.43, 132.38, 132.28, 132.15, 131.74, 131.64, 131.51, 130.99, 129.51, 128.37, 128.24, 128.13, 128.01, 127.93, 126.81, 54.36 (CH), 31.38 (d, J=3.7 Hz, CH₂), 10.49 (CH₃).

<3.9. Experimental Procedure of Entry 9>

The experimental procedure of this entry was the same as that illustrated in entry 1, except that the imines 8i was used in this entry as a reactant and the reaction time of this entry was 30 hours to yield the adduct 9i.

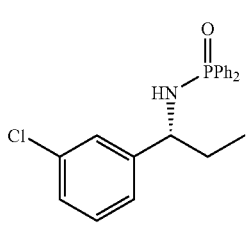

9i

¹H NMR (400 MHz, CDCl₃) δ 7.84-7.79 (m, 2H), 7.71-7.66 (m, 2H), 7.46-7.35 (m, 4H), 7.30-7.26 (m, 2H), 7.15-7.12 (m, 2H), 7.09 (s, 1H), 7.01-6.97 (m, 1H), 4.07-3.98 (m, 1H), 3.42-3.38 (m, 1H), 1.97-1.88 (m, 1H), 1.82-1.71 (m, 1H), 0.76 (t, J=7.2 Hz, 3H); ¹³C NMR (100 MHz, CDCl₃) δ 145.65 (d, J=5.1 Hz, C), 134.13, 133.48, 132.44, 132.35, 132.21, 131.78, 131.68, 129.62, 128.48, 128.35, 128.25, 128.12, 127.11, 126.63, 124.83, 56.56 (CH), 32.25 (d, J=3.6 Hz, CH₂), 10.46 (CH₃).

<3.10. Experimental Procedure of Entry 10>

The experimental procedure of this entry was the same as that illustrated in entry 1, except that the imines 8j was used in this entry as a reactant and the reaction time of this entry was 25 hours to yield the adduct 9j.

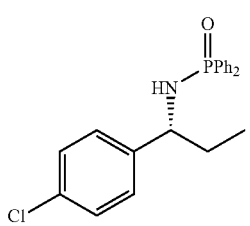

9j

¹H NMR (400 MHz, CDCl₃) δ 7.84-7.79 (m, 2H), 7.72-7.66 (m, 2H), 7.48-7.36 (m, 4H), 7.32-7.27 (m, 2H), 7.24-7.19 (m, 2H), 7.06-7.04 (m, 2H), 4.08-4.0 (m, 1H), 3.29-3.25 (m, 1H), 2.0-1.88 (m, 1H), 1.81-1.70 (m, 1H), 0.76 (t, J=7.2 Hz, 3H); ¹³C NMR (100 MHz, CDCl₃) δ 142.06 (d, J=5.1 Hz, C), 133.53, 132.66, 132.45, 132.36, 132.27, 131.82, 131.73, 131.24, 128.50, 128.40, 128.33, 128.20, 127.92, 56.43 (CH), 32.33 (d, J=4.4 Hz, CH₂), 10.46 (CH₃).

<3.11. Experimental Procedure of Entry 11>

The experimental procedure of this entry was the same as that illustrated in entry 1, except that the imines 8k was used in this entry as a reactant and the reaction time of this entry was 25 hours to yield the adduct 9k.

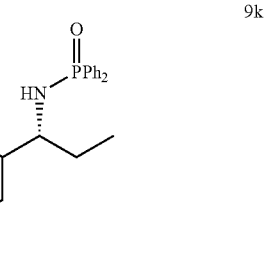

9k

¹H NMR (400 MHz, CDCl₃) δ 7.92-7.90 (m, 2H), 7.84-7.79 (m, 2H), 7.70-7.65 (m, 2H), 7.47-7.43 (m, 1H), 7.41-7.36 (m, 3H), 7.28-7.24 (m, 2H), 7.20-7.17 (m, 2H), 4.17-4.05 (m, 1H), 3.87 (s, 3H), 3.39-3.35 (m, 1H), 2.01-1.90 (m, 1H), 1.84-1.74 (m, 1H), 0.77 (t, J=7.2 Hz, 3H); ¹³C NMR (100 MHz, CDCl₃) δ 166.84 (C=O), 148.82 (d, J=5.1 Hz, C), 133.51, 132.46, 132.36, 131.88, 131.85, 131.81, 131.72, 131.13, 129.74, 128.88, 128.52, 128.39, 128.31, 128.18, 126.51, 56.73 (CH), 52.01 (CH₃), 32.36 (d, J=3.6 Hz, CH₂), 10.41 (CH₃).

<3.12. Experimental Procedure of Entry 12>

The experimental procedure of this entry was the same as that illustrated in entry 1, except that the imines 8l was used in this entry as a reactant and the reaction time of this entry was 120 hours to yield the adduct 9l.

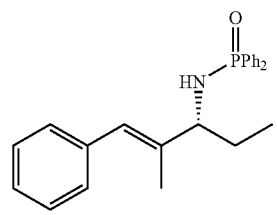

9l

¹H NMR. (400 MHz, CDCl₃) δ 7.92-7.84 (m, 4H), 7.47-7.35 (m, 6H), 7.29-7.25 (m, 2H), 7.18-7.15 (m, 1H), 7.11-7.09 (m, 2H), 6.06 (s, 1H), 3.66-3.58 (m, 1H), 3.10-3.06 (m, 1H), 1.82-1.73 (m, 1H), 1.77 (s, 3H), 1.70-1.61 (m, 1H), 0.87 (t, J=7.6 Hz, 3H); ¹³C NMR (100 MHz, CDCl₃) δ 137.91, 137.87, 137.47, 133.75, 132.93, 132.57, 132.47, 131.74, 131.64, 128.78, 128.42, 128.30, 128.23, 128.10, 127.87, 127.03, 126.21, 60.66 (CH), 28.91 (d, J=5.1 Hz, CH₂), 12.89 (CH₃), 10.55 (CH₃).

<3.13. Experimental Procedure of Entry 13>

To a 10 mL round-bottomed flask were added imine 8l (0.34 mmol) and amino alcohol 7 (0.0766 g, 0.34 mmol) in toluene (3 mL), followed by the addition of a diethylzinc solution (1.0 M in n-hexane, 1.7 mL, 1.7 mmol) under ice-bath condition. The reaction solution was stirred for 144 hours at room temperature and then an ammonium chloride solution (1 N aqueous solution, 4 mL) was added thereto to stop the reaction. Subsequently, the reaction solution was acidified (pH=2) by $HCl_{(aq)}$ (1 N) and separated into an organic layer and an aqueous layer. The aqueous layer was extracted with dichlormethane (10 mL×3) and the organic layer was dried over $Na_2SO_4$ (anhydrous), filtered and concentrated, to give the crude product, which was purified by column chromatography (methanol:dichlormethane=1:40-1:20 as a eulation) to yield the adduct 91.

<3.14. Experimental Procedure of Entry 14>

To a 10 mL round-bottomed flask were added imine 8a (0.34 mmol) and amino alcohol 7 (0.0766 g, 0.34 mmol) in toluene (3 mL), followed by the addition of a dimethylzinc solution (1.0 wt % in n-hexane, 2.2 mL, 1.7 mmol) under ice-bath condition. The reaction solution was stirred for 24 hours at room temperature and then an ammonium chloride solution (1 N aqueous solution, 4 mL) was added thereto to stop the reaction. Subsequently, the reaction solution was acidified (pH=2) by $HCl_{(aq)}$ (1 N) and separated into an organic layer and an aqueous layer. The aqueous layer was extracted with dichlormethane (10 mL×3) and the organic layer was dried over $Na_2SO_4$ (anhydrous), filtered and concentrated, to give the crude product, which was purified by column chromatography (methanol:dichlormethane=1:40-1:20 as a eulation) to yield the adduct 9a'.

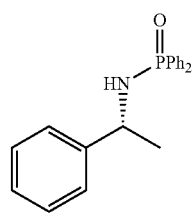

9a'

$^1$H NMR (400 MHz, $CDCl_3$) δ 7.90-7.85 (m, 2H), 7.82-7.76 (m, 2H), 7.47-7.37 (m, 4H), 7.35-7.30 (m, 2H), 7.29-7.18 (m, 5H), 4.41-4.31 (m, 1H), 3.25-3.24 (m, 1H), 1.54 (d, J=6.8 Hz, 3H); $^{13}$C NMR (100 MHz, $CDCl_3$) δ 144.99 (d, J=6.6 Hz, C), 133.75, 132.40, 131.89, 131.79, 131.74, 131.68, 131.66, 131.41, 128.48, 128.46, 128.37, 128.34, 128.25, 127.02, 125.87, 50.96 (CH), 25.9 (d, J=2.9 Hz, $CH_3$).

<3.15. Experimental Procedure of Entry 15>

The experimental procedure of this entry was the same as that illustrated in entry 14, except that the imines 8d was used in this entry as a reactant to yield the adduct 9d'.

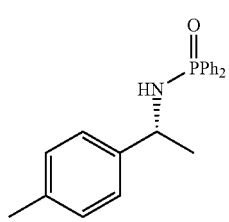

9d'

$^1$H NMR (400 MHz, $CDCl_3$) δ 7.90-7.85 (m, 2H), 7.83-7.8 (m, 2H), 7.47-7.31 (m, 6H), 7.16-7.14 (m, 2H), 7.10-7.08 (m, 2H), 4.37-4.27 (m, 1H), 3.23-3.20 (m, 1H), 2.3 (s, 3H), 1.53 (d, J=6.4 Hz, 3H); $^{13}$C NMR (100 MHz, $CDCl_3$) δ 142.10 (d, J=6.6 Hz, C), 136.62, 133.80, 132.79, 132.41, 132.31, 131.89, 131.80, 131.73, 131.65, 131.49, 129.14, 128.45, 128.37, 128.32, 128.25, 125.78, 50.74 (CH), 25.87 (d, J=2.9 Hz, $CH_3$), 20.96 ($CH_3$).

<3.16. Experimental Procedure of Entry 16>

The experimental procedure of this entry was the same as that illustrated in entry 14, except that the imines 8g was used in this entry as a reactant to yield the adduct 9g'.

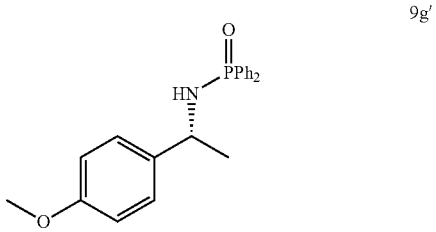

9g'

$^1$H NMR (400 MHz, $CDCl_3$) δ 7.89-7.84 (m, 2H), 7.82-7.76 (m, 2H), 7.47-7.31 (m, 6H), 7.20-7.16 (m, 2H), 6.82-6.79 (m, 2H), 4.36-4.27 (m, 1H), 3.75 (s, 3H), 3.21-3.17 (m, 1H), 1.52 (d, J=6.4 Hz, 3H); $^{13}$C NMR (100 MHz, $CDCl_3$) δ 158.54, 137.25, 137.18, 132.54, 132.37, 131.89, 131.80, 131.72, 131.69, 131.64, 131.62, 131.58, 128.44, 128.36, 128.31, 128.23, 127.05, 113.80, 55.19 ($CH_3$), 50.39 (CH), 25.76 ($CH_3$).

<3.17. Experimental Procedure of Entry 17>

The experimental procedure of this entry was the same as that illustrated in entry 14, except that the imines 8k was used in this entry as a reactant to yield the adduct 9k'.

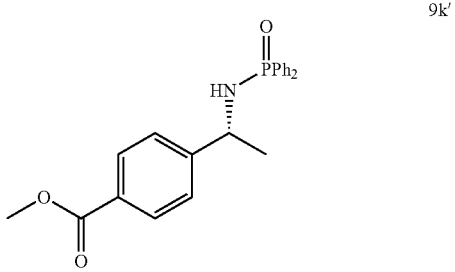

9k'

$^1$H NMR (400 MHz, $CDCl_3$) δ 7.88-7.86 (m, 2H), 7.83-7.78 (m, 2H), 7.71-7.66 (m, 2H), 7.41-7.36 (m, 1H), 7.34-7.22 (m, 7H), 4.38-4.28 (m, 1H), 3.80 (s, 3H), 3.76-3.72 (m, 1H), 1.49 (t, J=6.8 Hz, 3H); $^{13}$C NMR (100 MHz, $CDCl_3$) δ 166.66, 150.22 (d, J=5.9 Hz, C), 133.37, 132.57, 132.16, 132.06, 131.78, 131.68, 131.59, 131.56, 131.28, 129.65, 128.61, 128.34, 128.23, 128.10, 125.88, 51.83 ($CH_3$), 50.60 (CH), 25.64 (d, J=3.7 Hz, $CH_3$).

The above examples are intended for illustrating the embodiments of the subject invention and the technical features thereof, but not for restricting the scope of protection of the subject invention. The scope of the subject invention is based on the claims as appended.

What is claimed is:

1. A method of enantioselective addition to imines, comprising: reacting $R_3CH{=}NY$ with $R_4ZnR_5$ in the presence of a compound represented by the following formula (I),

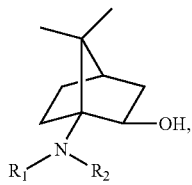

(I)

wherein
each of $R_1$ and $R_2$ independently is alkyl, or $R_1$ and $R_2$ taken together is $(CH_2)_mX(CH_2)_n$;
each of $R_3$, $R_4$ and $R_5$, independently, is alkyl, alkenyl, cycloalkyl, cycloalkenyl, heterocycloalkyl, heterocycloalkenyl, aryl, or heteroaryl;
X is O, S or $CH_2$;
Y is $P(O)Ph_2$; and
each of m and n, independently, is 1, 2 or 3, and the sum of m and n is 3 or 4.

2. The method as claimed in claim 1, wherein each of $R_1$ and $R_2$ independently is $C_{1-30}$ alkyl, or $R_1$ and $R_2$ taken together is $(CH_2)_mX(CH_2)_n$;

$R_3$ is unsubstituted or substituted $C_{1-30}$ alkyl by one or more selected from the group consisting of halogen, cyano, $C_{1-30}$ alkoxy, $C_{1-30}$ haloalkyl, $CO_2$—$C_{1-30}$ alkyl, $CO_2$—$C_{2-30}$ alkenyl, $C_{6-14}$ aryl and 5-14 membered heteroaryl; $(CH_2)_iR_a$; unsubstituted or substituted $C_{2-30}$ alkenyl by one or more selected from the group consisting of halogen, cyano, $C_{1-30}$ alkoxy, $C_{1-30}$ haloalkyl, $CO_2$—$C_{1-30}$ alkyl, $CO_2$—$C_{2-30}$ alkenyl, $C_{6-14}$ aryl and 5-14 membered heteroaryl; $(CH_2)_rCH=CH(CH_2)_kR_a$; unsubstituted or substituted $C_{5-14}$ cycloalkyl by one or more selected from the group consisting of halogen, cyano, $C_{1-30}$ alkyl, $C_{2-30}$ alkenyl, $C_{1-30}$ alkoxy, $C_{1-30}$ haloalkyl, $CO_2$—$C_{1-30}$ alkyl and $CO_2$—$C_{2-30}$ alkenyl; unsubstituted or substituted $C_{5-14}$ cycloalkenyl by one or more selected from the group consisting of halogen, cyano, $C_{1-30}$ alkyl, $C_{2-30}$ alkenyl, $C_{1-30}$ alkoxy, $C_{1-30}$ haloalkyl, $CO_2$—$C_{1-30}$ alkyl and $CO_2$—$C_{2-30}$ alkenyl; unsubstituted or substituted 5-14 membered heterocycloalkyl by one or more selected from the group consisting of halogen, cyano, $C_{1-30}$ alkyl, $C_{2-30}$ alkenyl, $C_{1-30}$ alkoxy, $C_{1-30}$ haloalkyl, $CO_2$—$C_{1-30}$ alkyl and $CO_2$—$C_{2-30}$ alkenyl; unsubstituted or substituted 5-14 membered heterocycloalkenyl by one or more selected from the group consisting of halogen, cyano, $C_{1-30}$ alkyl, $C_{2-30}$ alkenyl, $C_{1-30}$ alkoxy, $C_{1-30}$ haloalkyl, $CO_2$—$C_{1-30}$ alkyl and $CO_2$—$C_{2-30}$ alkenyl; unsubstituted or substituted $C_{6-14}$ aryl by one or more selected from the group consisting of halogen, cyano, $C_{1-30}$ alkyl, $C_{2-30}$ alkenyl, $C_{1-30}$ alkoxy, $C_{1-30}$ haloalkyl, $CO_2$—$C_{1-30}$ alkyl and $CO_2$—$C_{2-30}$ alkenyl; or unsubstituted or substituted 5-14 membered heteroaryl by one or more selected from the group consisting of halogen, cyano, $C_{1-30}$ alkyl, $C_{2-30}$ alkenyl, $C_{1-30}$ alkoxy, $C_{1-30}$ haloalkyl, $CO_2$—$C_{1-30}$ alkyl and $CO_2$—$C_{2-30}$ alkenyl;

each of $R_4$ and $R_5$ independently is unsubstituted or substituted $C_{1-30}$ alkyl by one or more of halogen, cyano, $C_{1-30}$ alkoxy, $C_{1-30}$ haloalkyl, $CO_2$—$C_{1-30}$ alkyl, $CO_2$—$C_{2-30}$ alkenyl, $C_{6-14}$ aryl and 5-14 membered heteroaryl; unsubstituted or substituted $C_{2-30}$ alkenyl by one or more of halogen, cyano, $C_{1-30}$ alkoxy, $C_{1-30}$ haloalkyl, $CO_2$—$C_{1-30}$ alkyl, $CO_2$—$C_{2-30}$ alkenyl, $C_{6-14}$ aryl and $C_{5-14}$ heteroaryl; unsubstituted or substituted $C_{5-14}$ cycloalkyl by one or more of halogen, cyano, $C_{1-30}$ alkyl, $C_{2-30}$ alkenyl, $C_{1-30}$ alkoxy, $C_{1-30}$ haloalkyl $CO_2$—$C_{1-30}$ alkyl and $CO_2$—$C_{2-30}$ alkenyl; unsubstituted or substituted $C_{5-14}$ cycloalkenyl by one or more of halogen, cyano, $C_{1-30}$ alkyl, $C_{2-30}$ alkenyl, $C_{1-30}$ alkoxy, $C_{1-30}$ haloalkyl, $CO_2$—$C_{1-30}$ alkyl and $CO_2$—$C_{2-30}$ alkenyl; unsubstituted or substituted 5-14 membered heterocycloalkyl by one or more of halogen, cyano, $C_{1-30}$ alkyl, $C_{2-30}$ alkenyl, $C_{1-30}$ alkoxy, $C_{1-30}$ haloalkyl, $CO_2$—$C_{1-30}$ alkyl and $CO_2$—$C_{2-30}$ alkenyl; unsubstituted or substituted 5-14 membered heterocycloalkenyl by one or more of halogen, cyano, $C_{1-30}$ alkyl, $C_{2-30}$ alkenyl, $C_{1-30}$ alkoxy, $C_{1-30}$ haloalkyl, $CO_2$—$C_{1-30}$ alkyl and $CO_2$—$C_{2-30}$ alkenyl; unsubstituted or substituted $C_{6-14}$ aryl by one or more of halogen, cyano, $C_{1-30}$ alkyl, $C_{2-30}$ alkenyl, $C_{1-30}$ alkoxy, $C_{1-30}$ haloalkyl, $CO_2$—$C_{1-30}$ alkyl and $CO_2$—$C_{2-30}$ alkenyl; or unsubstituted or substituted 5-14 membered heteroaryl by one or more of halogen, cyano, $C_{1-30}$ alkyl, $C_{2-30}$ alkenyl, $C_{1-30}$ alkoxy, $C_{1-30}$ haloalkyl, $CO_2$—$C_{1-30}$ alkyl and $CO_2$—$C_{2-30}$ alkenyl;

$R_a$ is substituted $C_{6-14}$ aryl by one or more selected from the group consisting of halogen, cyano, $C_{1-30}$ alkyl, $C_{2-30}$ alkenyl, $C_{1-30}$ alkoxy, $C_{1-30}$ haloalkyl, $CO_2$—$C_{1-30}$ alkyl and $CO_2$—$C_{2-30}$ alkenyl; or substituted 5-14 membered heteroaryl by one or more selected from the group consisting of halogen, cyano, $C_{1-30}$ alkyl, $C_{2-30}$ alkenyl, $C_{1-30}$ alkoxy, $C_{1-30}$ haloalkyl, $CO_2$—$C_{1-30}$ alkyl and $CO_2$—$C_{2-30}$ alkenyl;

i is an integer of 1 to 30; and
each of r and k independently is an integer of 0 to 30.

3. The method as claimed in claim 1, wherein each of $R_1$ and $R_2$ independently is $C_{1-10}$ alkyl, or $R_1$ and $R_2$ taken together is $(CH_2)_mX(CH_2)_n$;

$R_3$ is unsubstituted or substituted $C_{1-10}$ alkyl by one or more selected from the group consisting of $C_{6-14}$ aryl and 5-14 membered heteroaryl; $(CH_2)_iR_a$; unsubstituted or substituted $C_{2-10}$ alkenyl by one or more selected from the group consisting of $C_{6-14}$ aryl and 5-14 membered heteroaryl; $(CH_2)_rCH=CH(CH_2)_kR_a$; unsubstituted $C_{5-14}$ cycloalkyl; unsubstituted $C_{5-14}$ cycloalkenyl; unsubstituted or substituted $C_{6-14}$ aryl by one or more selected from the group consisting of halogen, cyano, $C_{1-10}$ alkyl, $C_{2-10}$ alkenyl, $C_{1-10}$ alkoxy, $C_{1-10}$ haloalkyl, $CO_2$—$C_{1-10}$ alkyl and $CO_2$—$C_{2-10}$ alkenyl; or unsubstituted or substituted 5-14 membered heteroaryl by one or more selected from the group consisting of halogen, cyano, $C_{1-10}$ alkyl, $C_{2-10}$ alkenyl, $C_{1-10}$ alkoxy, $C_{1-10}$ haloalkyl, $CO_2$—$C_{1-10}$ alkyl and $CO_2$—$C_{2-10}$ alkenyl;

$R_4$ is unsubstituted $C_{1-10}$ alkyl;

$R_5$ is unsubstituted or substituted $C_{1-10}$ alkyl by one or more selected from the group consisting of $C_{6-14}$ aryl and 5-14 membered heteroaryl; unsubstituted or substituted $C_{2-10}$ alkenyl by one or more selected from the group consisting of $C_{6-14}$ aryl and 5-14 membered heteroaryl; unsubstituted $C_{5-14}$ cycloalkyl; unsubstituted $C_{5-14}$ cycloalkenyl; unsubstituted or substituted $C_{6-14}$ aryl by one or more selected from the group consisting of halogen, cyano, $C_{1-10}$ alkyl, $C_{2-10}$ alkenyl, $C_{1-10}$ alkoxy, $C_{1-10}$ haloalkyl, $CO_2$—$C_{1-10}$ alkyl and $CO_2$-$C_{2-10}$ alkenyl; unsubstituted or substituted 5-14 membered heteroaryl by one or more selected from the group consisting of halogen, cyano, $C_{1-10}$ alkyl, $C_{2-10}$ alkenyl, $C_{1-10}$ alkoxy, $C_{1-10}$ haloalkyl, $CO_2$—$C_{1-10}$ alkyl and $CO_2$—$C_{2-10}$ alkenyl;

$R_a$ is substituted $C_{6-14}$ aryl by one or more selected from the group consisting of halogen, cyano, $C_{1-10}$ alkyl, $C_{2-10}$ alkenyl, $C_{1-10}$ alkoxy, $C_{1-10}$ haloalkyl, $CO_2$—$C_{1-10}$ alkyl and $CO_2$—$C_{2-10}$ alkenyl; or substituted 5-14 membered heteroaryl by one or more selected from the group consisting of halogen, cyano, $C_{1-10}$ alkyl, $C_{2-10}$ alkenyl, $C_{1-10}$ alkoxy, $C_{1-10}$ haloalkyl, $CO_2$—$C_{1-10}$ alkyl and $CO_2$—$C_{2-10}$ alkenyl;

i is an integer of 1 to 10; and each of r and k independently is an integer of 0 to 10.

4. The method as claimed in claim 3, wherein the sum of m and n is 4 when X is O or S.

5. The method as claimed in claim 4, wherein m is 1 or 2, and n is 2.

6. The method as claimed in claim 1, wherein each of $R_1$ and $R_2$ independently is $C_{1-10}$ alkyl, or $R_1$ and $R_2$ taken together is $(CH_2)_4$, $(CH_2)_5$ or $(CH_2)_2O(CH_2)_2$.

7. The method as claimed in claim 1, wherein the compound represented by the formula (I) is used in an amount of 0.1 to 1 equivalent based on $R_3CH$=NY.

8. The method as claimed in claim 1, wherein $R_3CH$=NY is reacted with $R_4ZnR_5$ at a temperature in a range from 0° C. to 50° C.

9. The method as claimed in claim 1, wherein $R_4ZnR_5$ is used in an amount of 1 to 10 equivalents based on $R_3CH$=NY.

10. The method as claimed in claim 1, wherein $R_3CH$=NY is reacted with $R_4ZnR_5$ in an aprotic solvent.

11. The method as claimed in claim 10, wherein the concentration of $R_3CH$=NY in the aprotic solvent ranges from 0.01 M to 1 M.

12. The method as claimed in claim 11, wherein the aprotic solvent is selected from the group consisting of n-hexane, toluene, dichloromethane, tetrahydrofuran, acetonitrile, a mixture of n-hexane and toluene, a mixture of n-hexane and dichloromethane, a mixture of n-hexane and tetrahydrofuran, and a mixture of n-hexane and acetonitrile.

13. The method as claimed in claim 12, wherein the aprotic solvent is selected from the group consisting of n-hexane, toluene, a mixture of n-hexane and toluene in a ratio of 1:1 to 1:5, a mixture of n-hexane and dichloromethane in a ratio of 1:1 to 1:3, a mixture of n-hexane and tetrahydrofuran in a ratio of 1:1 to 1:3, and a mixture of n-hexane and acetonitrile in a ratio of 1:1 to 1:3.

* * * * *